US009346759B2

(12) United States Patent
Amat Mestres et al.

(10) Patent No.: US 9,346,759 B2
(45) Date of Patent: May 24, 2016

(54) POLYMORPHIC CRYSTAL FORMS OF 5-(2-{[6-(2,2-DIFLUORO-2-PHENYLETHOXY) HEXYL]AMINO}-1-(R)-HYDROXYETHYL)-8-HYDROXYQUINOLIN-2(1H)-ONE, HEMINAPADISYTLATE AS AGONIST OF THE β2 ADRENERGIC RECEPTOR

(71) Applicant: ALMIRALL, S.A., Barcelona (ES)

(72) Inventors: Gemma Amat Mestres, Sant Feliu de Llobregat (ES); Elvira Balaguer Ardanuy, Sant Feliu de Llobregat (ES); Francesc Carrera Carrera, Sant Feliu de Llobregat (ES); Iolanda Marchueta Hereu, Sant Feliu de Llobregat (ES); Enrique Moyes Valls, Sant Feliu de Llobregat (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 14/386,424

(22) PCT Filed: Mar. 15, 2013

(86) PCT No.: PCT/EP2013/055488
§ 371 (c)(1),
(2) Date: Sep. 19, 2014

(87) PCT Pub. No.: WO2013/139712
PCT Pub. Date: Sep. 26, 2013

(65) Prior Publication Data
US 2015/0057256 A1    Feb. 26, 2015

Related U.S. Application Data

(60) Provisional application No. 61/622,266, filed on Apr. 10, 2012.

(30) Foreign Application Priority Data

Mar. 20, 2012   (EP) .................................... 12382101

(51) Int. Cl.
*C07D 215/227* (2006.01)
*C07D 215/26* (2006.01)
*A61K 31/4704* (2006.01)
*A61K 45/06* (2006.01)

(52) U.S. Cl.
CPC ........ *C07D 215/227* (2013.01); *A61K 31/4704* (2013.01); *A61K 45/06* (2013.01); *C07D 215/26* (2013.01); *C07B 2200/13* (2013.01)

(58) Field of Classification Search
CPC ............. C07D 215/227; C07D 215/26; A61K 31/4704
See application file for complete search history.

(56) References Cited

U.S. PATENT DOCUMENTS

| 2,579,479 | A | 12/1951 | Djerassi et al. |
| 2,837,464 | A | 6/1958 | Nobile |
| 2,897,216 | A | 7/1959 | Oliveto et al. |
| 3,007,923 | A | 11/1961 | Muller et al. |
| 3,053,865 | A | 9/1962 | Taub et al. |
| 3,104,246 | A | 9/1963 | Amiard et al. |
| 3,134,718 | A | 5/1964 | Nobile |
| 3,678,137 | A | 7/1972 | Pfeiffer et al. |
| 3,929,768 | A | 12/1975 | Brattsand et al. |
| 3,970,677 | A | 7/1976 | Nishimura et al. |
| 3,975,391 | A | 8/1976 | Nakagawa et al. |
| 3,983,233 | A | 9/1976 | Brattsand et al. |
| 3,994,901 | A | 11/1976 | Nakagawa et al. |
| 4,022,776 | A | 5/1977 | Nakagawa et al. |
| 4,022,784 | A | 5/1977 | Nakagawa et al. |
| 4,026,897 | A | 5/1977 | Nakagawa et al. |
| 4,068,076 | A | 1/1978 | Nakagawa et al. |
| 4,145,542 | A | 3/1979 | Nakagawa et al. |
| 4,254,129 | A | 3/1981 | Carr et al. |
| 4,254,130 | A | 3/1981 | Carr et al. |
| 4,753,962 | A | 6/1988 | Ainsworth et al. |
| 4,992,474 | A | 2/1991 | Skidmore et al. |
| 4,997,986 | A | 3/1991 | Mitchell et al. |
| 5,099,068 | A | 3/1992 | Mitchell et al. |
| 5,109,023 | A | 4/1992 | Mitchell et al. |
| 5,201,308 | A | 4/1993 | Newhouse |
| 5,263,475 | A | 11/1993 | Altermatt et al. |
| 5,283,262 | A | 2/1994 | Mitchell et al. |
| 5,435,301 | A | 7/1995 | Herold et al. |
| 5,482,934 | A | 1/1996 | Calatayud et al. |
| 5,507,281 | A | 4/1996 | Kuhnel et al. |

(Continued)

FOREIGN PATENT DOCUMENTS

| DE | 1 113 690 | 2/1958 |
| DE | 2 236 272 | 2/1973 |

(Continued)

OTHER PUBLICATIONS

U.S. Appl. No. 11/920,561, filed Feb. 11, 2008, Puig Duran et al.
U.S. Appl. No. 12/298,131, filed Nov. 10, 2008, Puig Duran et al.
U.S. Appl. No. 12/444,935, filed May 14, 2009, Bach Taña et al.
U.S. Appl. No. 12/526,090, filed Oct. 8, 2009, Puig Duran et al.
U.S. Appl. No. 12/745,195, filed May 27, 2010, Giulio Matassa et al.
U.S. Appl. No. 12/919,134, filed Oct. 7, 2010, Puig Duran et al.
U.S. Appl. No. 13/141,156, filed Jun. 21, 2011, Carrera Carrera et al.

(Continued)

*Primary Examiner* — D M Seaman
(74) *Attorney, Agent, or Firm* — Finnegan, Henderson, Farabow Garrett & Dunner LLP

(57) ABSTRACT

The present invention is directed to novel polymorphic crystal forms of a 5-(2-{[6-(2,2-difluoro-2-phenylethoxy)hexyl]amino}-1-(R)-hydroxyethyl)-8-hydroxyquinolin-2(1H)-one, heminapadisylate. The invention is also directed to pharmaceutical compositions comprising said polymorphic crystal forms, methods of using them to treat respiratory diseases associated with β2 adrenergic receptor activity and a process for preparing such polymorphic crystal forms.

31 Claims, 9 Drawing Sheets

(56) References Cited

U.S. PATENT DOCUMENTS

| | | |
|---|---|---|
| 5,617,845 A | 4/1997 | Poss et al. |
| 5,648,370 A | 7/1997 | Bonnert et al. |
| 5,685,294 A | 11/1997 | Gupte et al. |
| 6,541,669 B1 | 4/2003 | Moran et al. |
| 7,498,321 B2 | 3/2009 | Biggadike et al. |
| 7,964,615 B2 | 6/2011 | Puig Duran et al. |
| 8,178,679 B2 | 5/2012 | Matassa et al. |
| 8,242,177 B2 | 8/2012 | Puig Duran et al. |
| 8,283,342 B2 | 10/2012 | Puig Duran et al. |
| 8,420,669 B2 | 4/2013 | Puig Duran et al. |
| 8,524,908 B2 | 9/2013 | Marchueta Hereu et al. |
| 8,563,731 B2 | 10/2013 | Carrera et al. |
| 2002/0055651 A1 | 5/2002 | Moran et al. |
| 2003/0136405 A1 | 7/2003 | Goede et al. |
| 2003/0153597 A1 | 8/2003 | Moran et al. |
| 2004/0059116 A1 | 3/2004 | Moran et al. |
| 2004/0167167 A1 | 8/2004 | Mammen et al. |
| 2005/0043337 A1 | 2/2005 | Rito et al. |
| 2005/0148563 A1 | 7/2005 | Cuss et al. |
| 2005/0159448 A1 | 7/2005 | McKinnell et al. |
| 2005/0192316 A1 | 9/2005 | Moran et al. |
| 2005/0215590 A1 | 9/2005 | Brown et al. |
| 2005/0272769 A1 | 12/2005 | Linsell |
| 2006/0019991 A1 | 1/2006 | McKinnell et al. |
| 2006/0035931 A1 | 2/2006 | Chao et al. |
| 2006/0081246 A1 | 4/2006 | Goede et al. |
| 2006/0178410 A1 | 8/2006 | Moran et al. |
| 2006/0205949 A1 | 9/2006 | Dalziel et al. |
| 2007/0197536 A1 | 8/2007 | Dal Piaz et al. |
| 2009/0042933 A1 | 2/2009 | Duran et al. |
| 2009/0082378 A1 | 3/2009 | Puig Duran et al. |
| 2010/0093681 A1 | 4/2010 | Puig Duran et al. |
| 2010/0168161 A1 | 7/2010 | Taña et al. |
| 2010/0324000 A1 | 12/2010 | Giulio Matassa et al. |
| 2011/0020454 A1 | 1/2011 | Lamarca Casado et al. |
| 2011/0028442 A1 | 2/2011 | Puig Duran et al. |
| 2011/0251165 A1 | 10/2011 | Puig Duran et al. |
| 2011/0251166 A1 | 10/2011 | Puig Duran et al. |
| 2011/0251234 A1 | 10/2011 | Carrera Carrera et al. |
| 2012/0004414 A1 | 1/2012 | Marchueta Hereu et al. |
| 2012/0029014 A1 | 2/2012 | Ruf et al. |
| 2012/0040941 A1 | 2/2012 | Ruf et al. |
| 2014/0038928 A1 | 2/2014 | Ruf et al. |
| 2014/0343097 A1 | 11/2014 | Ruf et al. |
| 2015/0065471 A1 | 3/2015 | Duran et al. |
| 2015/0140099 A1 | 5/2015 | Ruiz et al. |

FOREIGN PATENT DOCUMENTS

| | | |
|---|---|---|
| DE | 2 323 215 | 11/1973 |
| DE | 2 310 140 | 9/1974 |
| DE | 24 61 861 | 8/1975 |
| DE | 41 29 535 | 3/1992 |
| DE | 42 39 402 A1 | 5/1994 |
| EP | 0 057 401 | 8/1982 |
| EP | 0 069 715 A1 | 1/1983 |
| EP | 0 147 719 A2 | 7/1985 |
| EP | 0 166 294 A2 | 1/1986 |
| EP | 0 286 242 A2 | 10/1988 |
| EP | 0 317 206 A2 | 5/1989 |
| EP | 0 424 790 A2 | 5/1991 |
| EP | 0 505 321 A2 | 9/1992 |
| EP | 0 674 533 B1 | 3/1999 |
| EP | 1 078 629 A2 | 2/2001 |
| EP | 1 235 787 B1 | 10/2003 |
| EP | 1 577 291 A1 | 9/2005 |
| ES | 2 232 306 A1 | 5/2005 |
| GB | 0 869 511 | 5/1961 |
| GB | 1 200 886 | 8/1970 |
| GB | 1 247 370 | 9/1971 |
| GB | 1 458 251 | 12/1976 |
| GB | 1 468 156 | 3/1977 |
| GB | 2 041 763 A | 9/1980 |
| GB | 2 140 800 A | 12/1984 |
| GB | 2 160 863 A | 1/1986 |
| GB | 2 165 159 A | 4/1986 |
| GB | 2 242 134 A | 9/1991 |
| JP | 51-149282 A | 12/1976 |
| JP | 59-093051 A | 5/1984 |
| WO | WO 91/02558 A1 | 3/1991 |
| WO | WO 91/14468 A1 | 10/1991 |
| WO | WO 92/00771 A1 | 1/1992 |
| WO | WO 92/03175 A1 | 3/1992 |
| WO | WO 92/04068 A1 | 3/1992 |
| WO | WO 92/04928 A2 | 4/1992 |
| WO | WO 92/09322 A1 | 6/1992 |
| WO | WO 96/32150 A1 | 10/1996 |
| WO | WO 96/35667 | 11/1996 |
| WO | WO 97/00703 A1 | 1/1997 |
| WO | WO 97/12687 A1 | 4/1997 |
| WO | WO 98/09632 A1 | 3/1998 |
| WO | WO 99/30703 A1 | 6/1999 |
| WO | WO 99/64035 A1 | 12/1999 |
| WO | WO 01/36375 A1 | 5/2001 |
| WO | WO 01/42193 A1 | 6/2001 |
| WO | WO 02/066422 A1 | 8/2002 |
| WO | WO 02/070490 A1 | 9/2002 |
| WO | WO 02/092606 A1 | 11/2002 |
| WO | WO 03/000325 A1 | 1/2003 |
| WO | WO 03/042160 A1 | 5/2003 |
| WO | WO 03/061742 A2 | 7/2003 |
| WO | WO 03/072539 A1 | 9/2003 |
| WO | WO 03/091204 A1 | 11/2003 |
| WO | WO 03/097613 A1 | 11/2003 |
| WO | WO 03/099764 A1 | 12/2003 |
| WO | WO 2004/011416 A1 | 2/2004 |
| WO | WO 2004/016578 A2 | 2/2004 |
| WO | WO 2004/058729 A1 | 7/2004 |
| WO | WO 2004/089892 A2 | 10/2004 |
| WO | WO 2004/106279 A2 | 12/2004 |
| WO | WO 2005/030678 A2 | 4/2005 |
| WO | WO 2005/040103 | 5/2005 |
| WO | WO 2005/042514 | 5/2005 |
| WO | WO 2005/049581 A1 | 6/2005 |
| WO | WO 2005/097804 | 10/2005 |
| WO | WO 2005/121065 A2 | 12/2005 |
| WO | WO 2005/123692 A1 | 12/2005 |
| WO | WO 2005/123693 A1 | 12/2005 |
| WO | WO 2006/023457 A1 | 3/2006 |
| WO | WO 2006/051375 A1 | 5/2006 |
| WO | WO 2006/122788 A1 | 11/2006 |
| WO | WO 2007/106016 | 9/2007 |
| WO | WO 2007/124898 A1 | 11/2007 |
| WO | WO 2007/146715 | 12/2007 |
| WO | WO 2008/046598 A1 | 4/2008 |
| WO | 2008/095720 * | 8/2008 |
| WO | WO 2008/093188 | 8/2008 |
| WO | WO 2008/095720 | 8/2008 |
| WO | WO 2008/131932 | 11/2008 |
| WO | WO 2008/135819 | 11/2008 |
| WO | WO 2009/026408 | 2/2009 |
| WO | WO 2009/026584 | 2/2009 |
| WO | WO 2009/032764 | 3/2009 |
| WO | WO 2009/068177 A1 | 6/2009 |
| WO | WO 2009/106351 A1 | 9/2009 |
| WO | WO 2010/072354 | 7/2010 |
| WO | WO 2010/094483 A1 | 8/2010 |
| WO | WO 2010/094484 A1 | 8/2010 |
| WO | WO 2010/102831 | 9/2010 |
| WO | WO 2013/050375 A1 | 4/2013 |
| WO | WO 2013/139712 | 9/2013 |
| WO | WO 2013/149959 | 10/2013 |

OTHER PUBLICATIONS

U.S. Appl. No. 13/094,163, filed Apr. 26, 2011, Puig Duran et al.
U.S. Appl. No. 13/202,020, filed Oct. 18, 2011, Ruf et al.
U.S. Appl. No. 13/202,025, filed Oct. 14, 2011, Ruf et al.
U.S. Appl. No. 13/255,621, filed Sep. 19, 2011, Marchueta Hereu et al.
U.S. Appl. No. 13/428,450, filed Mar. 23, 2012, Giulio Matassa et al.
U.S. Appl. No. 13/538,117, filed Jun. 29, 2012, Bach Taña et al.
U.S. Appl. No. 14/048,344, filed Oct. 8, 2013, Thorsten Ruf et al.
U.S. Appl. No. 14/225,849, filed Mar. 28, 2014, Thorsten Ruf et al.

(56) References Cited

OTHER PUBLICATIONS

U.S. Appl. No. 14/350,108, filed Apr. 7, 2014, Iolanda Marchueta Hereu et al.
U.S. Appl. No. 14/389,843, filed Oct. 1, 2014, Carlos Puid Duran et al.n.
Bateman, E.D. et al. "Global strategy for asthma management and prevention: GINA executive summary," Eur Resp J., 31(1):143-178 (2008).
Bastin, R.D. et al. "Salt Selection and Optimisation for Pharmaceutical New Chemical Entities," *Organic Process Research and Development*, 4(5):427-435 (2000).
Berge, S.M. et al. "Pharmaceutical salts," Journal of Pharmaceutical Sciences, 1977, 66(1), pp. 1-19.
Budesonide, Merck Index, Monograph No. 01468 (2012).
CAPLUS[SM] English Abstract of DE 2 236 272, Accession No. 1973:405128.
CAPLUS[SM] English Abstract of DE 2 310 140, Accession No. 1975:31115.
CAPLUS[SM] English Abstract of journal article by De Meglio, P. et al., Accession No. 1980:426036.
CAPLUS[SM] English Abstract of JP 51 149 282, Accession No. 1977:468184.
CAPLUS[SM] English Abstract of JP 59 093 051, Accession No. 1985:45790.
Chowdhury, B.A. et al. "The risks and benefits of indacaterol—The FDA's review," New England Journal of Medicine, 2011, 365(24), pp. 2247-2249.
Ciclesonide, Merck Index, Monograph No. 02263 (2012).
Coleman, R.A. et al. "Novel and Versatile Superfusion System: Its Use in the Evolution of Some Spasmogenic and Spasmolytic Agents Using Guinea-pig Isolated Tracheal Smooth Muscle," *Journal of Pharmacological Methods*, 21:71-86 (1989).
Cortijo, J. et al. "Effects of dantrolene on the responses to methylxanthines in the isolated guinea-pig trachea," *European Journal of Pharmacology*, 198:171-176 (1991).
Curran, P.K. et al. "Endogenous $\beta_3$- But Not $\beta_1$-Adrenergic Receptors Are Resistant to Agonist-Mediated Regulation in Human SK-N-MC Neurotumor Cells," *Cell. Signal.*, 8(5):355-364 (1996).
Dahl, R. et al. "Efficacy of a new once-daily long-acting inhaled $\beta_2$-agonist indacaterol versus twice-daily formoterol in COPD," Thorax, 2010, 65, pp. 473-479.
De Meglio, P. et al. "Synthesis and pharmacological study of orciprenaline and salbutamol derivatives," *Farmaco, Edizione Scientifica*, 35(3): 203-230 (1980).
De Vires, F. et al. "Use of β2 Agonists and Rsk of Acute Myocardial Infarction in Patients with Hypertension," Brit. J. Clin. Pharmacol. 65:580:586, 2008.
Deyrup, M.D. et al. "Structure-affinity profile of 8-hydroxycarbostyril-based agonists that dissociate slowly from the $\beta_2$-adrenoceptor," *Naunyn-Schmiedeberg's Archives of Pharmacology*, 359:168-177(1999).
Dexamethasone, Merck Index, Monograph No. 02943 (2011).
Dixon A.E., "Long-acting β-agonists and asthma: The saga continues," Am. J. Resp. Criti. Care Med., 2011, 184, pp. 1220-1221.
English Abstract of WO 2002/92606, Accession No. 00958733, 2 pp. (Nov. 21, 2002).
English Translation for DE 1113690.
Feldman, G. et al. "Efficacy and safety of indacaterol 150 µg once-daily in COPD: a double-blind, randomised, 12-week study," Bio Med Central, 2010, 10(11), pp. 1-9.
Furuie, H. et al. "Suppressive effect of novel phosphodiesterase4 (PDE4) inhibitor ONO-6126 on TNF-α release was increased after repeated oral administration in healthy Japanese subjects," 13th ERS Annual Congress, Sep. 27, 2003, Vienna. *Eur. Resp. Journal*, 22(Supp. 45):Abstract 2557 (2003).
Han, J. "Advances in Characterization of Pharmaceutical Hydrates," *Trends in Bio/Pharmaceutical Industry*, 2(3):25-29 (2006).
Hart, D.J. "A Synthesis of (±)-Gephyrotoxin," *Journal of Organic Chemistry*, 46:3576-3578 (1981).
Hart, D.J. et al. "Total Syntheses of dl-Gephyrotoxin and dl-Dihydrogephyrotoxin," *J. Am. Chem. Soc.*, 105(5):1255-1263 (1983).
Hashima, H. et al. "Synthesis and Biological Activities of the Marine Byrozoan Alkaloids Convolutamines A, C and F, and Lutamides A and C," *Bioorganic & Medicinal Chemistry*, 8:1757-1766 (2000).
Hett, R. et al. "Enantioselective Synthesis of Salmeterol via Asymmetric Borane Reduction," *Tetrahedron Letters*, 35(50):9375-9378 (1994).
Hett, R. et al. "Large-Scale Synthesis of Enantio- and Diastereomerically Pure (R,R)-Formoterol," *Organic Process Research & Development*, 2(2):96-99 (1998).
International Search Report mailed Sep. 12, 2006, for International Application No. PCT/EP2006/004680.
International Search Report mailed Apr. 21, 2009, for International Application No. PCT/EP2009/001431.
International Search Report mailed Jun. 21, 2007, for International Application No. PCT/EP2007/003601.
International Search Report mailed Mar. 19, 2008, for International Application No. PCT/EP2007/008992.
International Search Report mailed Mar. 2, 2010, for International Application No. PCT/EP2009/008970.
International Search Report mailed Sep. 16, 2010, for International Application No. PCT/EP2010/001582.
International Search Report mailed May 27, 2010, for International Application No. PCT/EP2010/001026.
International Search Report mailed May 25, 2010, for International Application No. PCT/EP2010/001027.
International Search Report mailed May 28, 2008, for International Application No. PCT/EP2008/000975.
International Search Report mailed May 7, 2009, for International Application No. PCT/EP2008/00946.
International Search Report mailed Oct. 25, 2012, for International Application No. PCT/EP2012/069475.
International Search Report mailed Jun. 25, 2013, for International Application No. PCT/EP2013/055488.
International Search Report mailed May 13, 2013, for International Application No. PCT/EP2013/056786.
Ismail, F.M.D. "Important fluorinated drugs in experimental and clinical use," *Journal of Fluorine Chemistry* 118:27-33 (2002).
Jacobsen, J.R. et al. "A multivalent approach to the discovery of long-acting $\beta_2$-adrenoceptor agonists for the treatment of asthma and COPD," J. Bioorganic & Medicinal Chemistry Letters, 2012, 22, pp. 1213-1218.
Johnson, M. "Salmeterol," *Medicinal Research Reviews*, 15(3):225-257 (1995).
Kaiser, C. et al. "Adrenergic Agents. 1. Synthesis and Potential β-Adrenergic Agonist Activity of Some Catecholamine Analogs Bearing a Substituted Amino Functionality in the Meta Position," *J. Med. Chem.*, 17(1):49-57 (1974).
Kikkawa, H. et al. "Differential contribution of two serine residues of wild type and constitutively active $\beta_2$-adrenoreceptors to the interaction with $\beta_2$-selective agonists," *British Journal of Pharmacology*, 121:1059-1064 (1997).
Konzett, H. et al. "Versuchsanorduung zu Untersuchungen an der Bronchialmuskulatur," Arch. Exp. Path. Pharmacol. 195, 1940, pp. 71-75.
Konzett, H. et al. "Versuchsanorduung zu Untersuchungen an der Bronchialmuskulatur," Arch. Exp. Path. Pharmacol. 195, 1940, pp. 71-75. English Translation.
Meyers, A.I. et al. "Oxazolines. XI. Synthesis of Functionalized Aromatic and Aliphatic Acids. A Useful Protecting Group for Carboxylic Acids against Grignard and Hydride Reagents," *J. Org. Chem.*, 39(18): 2787-2793 (1974).
Meyers, A.I. et al. "Substitutions on 1-Methoxynaphthalenes via their Oxazoline Derivatives: A Convenient Route to 1-Substituted Naphthoic Acids," *Synthesis Communications*, 2:105-107 (1983).
Mometasone, Merck Index, Monograph No. 06241 (2012).
Morissette, S.L. et al. "High-Throughput Crystallization: Polymorphs, Salts, Co-Crystals and Solvates of Pharmaceutical Solids," *Advanced Drug Delivery Reviews*, 56:275-300 (2004).

(56) References Cited

OTHER PUBLICATIONS

Murase, K. et al. "New β-Adrenoreceptor Stimulants. Studies on 3-Acylamino-4-hydroxy-α-(N-substituted aminomethyl)benzyl Alcohols," *Chem. Pharm. Bull.*, 25(6):1368-1377 (1977).
Nielsen, K.G. et al. "Flow-dependent effect of formoterol dry-powder inhaled from the Aerolizer®," *Eur. Respir. J.*, 10:2105-2109 (1997).
Patani, G.A. et al. "Bioisosterism: A Rational Approach in Drug Design," *Chem. Rev.* 96:3147-3176 (1996).
Portoghese, P.S. "Stereochemical Studies on Medicinal Agents. 19. X-Ray Crystal Structures of Two (±)-Allylprodine Diastereomers. The Role of the Allyl Group in Conferring High Stereoselectivity and Potency at Analgetic Receptors," J. Med. Chem., 19(1):55-57 (1976).
Prednisone, Merck Index, Monograph No. 07722 (2012).
Quanjer, Ph.H. et al. "Lung Volumes and Forced Ventilatory Flows," Eur Resp J., 6(Suppl16):5-40 (1993).
Salpeter, S.R. et al., "Cardiovascular Effects of β-Agonists in Patients with Asthma and COPD: A Meta-Analysis" Chest, vol. 125, pp. 2309-2321 (2004).
Silverman, R.B. "The Organic Chemistry of Drug Design and Drug Action," Academic Press, Chapter 2, pp. 10-23 (1992).
Smart, B.E. "Fluorine substituent effects (on bioactivity)," *Journal of Fluorine Chemistry* 109:3-11 (2001).
Sterling, J. et al. "Novel Dual Inhibitors of AChE and MAO Derived from Hydroxy Aminoindan and Phenethylamine as Potential Treatment for Alzheimer's Disease," *J. Med. Chem.* 45(24):5260-5279 (2002).
STN Search Report, File CAPLUS, Accession No. 2003:875242 (2011).
Svenson, R. et al. "On the Hydrozirconation of Some Long-Chain Unsaturated Fatty Acid Oxazolines," *Chemica Scripta.* 19:149-153 (1982).
Van Noord, J.A. et al., "24-hour Bronchodilation following a single dose of the novel $\beta_2$-agonist olodaterol in COPD." J. Pulmonary Pharmacology & Therapeutics, 2011, 24, pp. 666-672.
Vippagunta, S.R. et al. "Crystalline Solids," *Advanced Drug Delivery Reviews* 48:3-26 (2001).
Williams, D.A. et al. (eds.) *FOYE's Principles of Medicinal Chemistry.* 5th Edition, Lippincott Williams & Wilkins, 2002; pp. 59-63.
Yang, Z. "Synthesis of new α,α,β,β-tetrafluoroesters," *Journal of Fluorine Chemistry* 125:763-765 (2004).
Yang, Z. et al. "A Novel and Practical Method for the Preparation of α,α-Difluoro Functionalized Esters," *J. Chem. Soc., Chem. Commun.* 3:233-234 (1992).
Yoshizaki, S. et al. "Sympathomimetic Amines Having a 3,4-Dihydrocarbostyril Nucleus," *Chemical and Pharmaceutical Bulletin* 26(5):1611-1614 (1978).
Yoshizaki, S. et al. "Sympathomimetic Amines Having a Carbostyril Nucleus," *J. Med. Chem.* 19(9):1138-1142 (1976).
U.S. Appl. No. 11/920,561: Restriction Requirement dated Mar. 16, 2010.
U.S. Appl. No. 11/920,561: Office Action dated Jun. 2, 2010.
U.S. Appl. No. 11/920,561: Interview Summary dated Jun. 11, 2010.
U.S. Appl. No. 11/920,561: Office Action (Quayle Action) dated Nov. 9, 2010.
U.S. Appl. No. 11/920,561: Notice of Allowance dated Jan. 26, 2011.
U.S. Appl. No. 12/298,131: Office Action dated Apr. 25, 2011.
U.S. Appl. No. 12/298,131: Office Action dated Jan. 26, 2012.
U.S. Appl. No. 12/444,935: Restriction Requirement dated May 13, 2011.
U.S. Appl. No. 12/444,935: Office Action dated Jul. 7, 2011.
U.S. Appl. No. 12/444,935: Office Action dated Jan. 30, 2012.
U.S. Appl. No. 12/444,935: Office Action (Advisory Action) dated Jun. 4, 2012.
U.S. Appl. No. 12/745,195: Restriction Requirement dated Jan. 5, 2011.
U.S. Appl. No. 12/745,195: Office Action dated Mar. 9, 2011.
U.S. Appl. No. 12/745,195: Office Action dated Jul. 15, 2011.
U.S. Appl. No. 12/745,195: Interview Summary dated Feb. 22, 2012.
U.S. Appl. No. 12/745,195: Notice of Allowance dated Feb. 24, 2012.
U.S. Appl. No. 12/745,195: Notice of Allowance dated Dec. 28, 2011.
U.S. Appl. No. 13/094,156: Restriction Requirement dated Dec. 29, 2011.
U.S. Appl. No. 13/094,156: Office Action (Quayle Action) dated Feb. 14, 2012.
U.S. Appl. No. 13/094,156, Notice of Allowance dated Apr. 18, 2012.
U.S. Appl. No. 13/094,163: Office Action (Restriction Requirement) dated Jul. 6, 2012.
U.S. Appl. No. 13/094,163: Office Action dated Aug. 20, 2012.
U.S. Appl. No. 13/094,163: Notice of Allowance dated Dec. 12, 2012.
U.S. Appl. No. 12/526,090: Restriction Requirement dated Jul. 20, 2011.
U.S. Appl. No. 12/526,090: Office Action dated Oct. 14, 2011.
U.S. Appl. No. 12/526,090: Office Action dated Apr. 24, 2012.
U.S. Appl. No. 12/526,090: Interview Summary dated Jun. 26, 2012.
U.S. Appl. No. 12/526,090: Notice of Allowance dated Jun. 26, 2012.
U.S. Appl. No. 13/141,156 Notice of Allowance dated Jun. 21, 2013.
U.S. Appl. No. 13/202,020: Restriction Requirement dated Oct. 2, 2012.
U.S. Appl. No. 13/202,020: Office Action dated Apr. 8, 2013.
U.S. Appl. No. 13/202,025: Restriction Requirement dated Oct. 4, 2012.
U.S. Appl. No. 13/202,025: Office Action dated Apr. 17, 2013.
U.S. Appl. No. 13/202,025: Office Action dated Oct. 1, 2013.
U.S. Appl. No. 13/202,025: Interview Summary dated Mar. 10, 2014.
U.S. Appl. No. 13/255,621: Notice of Allowance dated May 10, 2013.
U.S. Appl. No. 14/048,344: Restriction Requirement dated Feb. 27, 2014.
U.S. Appl. No. 14/048,344: Office Action dated Oct. 23, 2014.
U.S. Appl. No. 14/389,843: Restriction Requirement dated Jan. 2, 2015.
U.S. Appl. No. 14/350,108: Notice of Allowance dated Feb. 2, 2015.
International Search Report for International Application No. PCT/EP2013/055488, Jun. 25, 2013.
Chrystyn, H. and Niederlaender, C.. "The Genuair® inhaler: a novel, multidose dry powder inhaler," The International Journal of Clinical Practice, vol. 66, No. 3, pp. 309-317 (2012).
International Search Report dated Aug. 1, 2013, for International Application No. PCT/EP2013/061181.
Saal, C. and Becker, A. "Pharmaceutical salts: A summary on doses of salt formers from the Orange Book," Eur J of Pharma Sci. 49:614-623 (2013).
U.S. Appl. No. 14/404,199, filed Nov. 26, 2014.
U.S. Appl. No. 14/404,199, Office Action dated Apr. 9, 2015.
U.S. Appl. No. 14/389,843, Office Action dated Apr. 23, 2015.
U.S. Appl. No. 14/350,108, Notice of Allowance dated May 20, 2015.

\* cited by examiner

Figure 1: X-Ray Powder Diffraction (XRPD) pattern of Type β polymorph of 5-(2-(6-(2,2-Difluoro-2-phenylethoxy)hexylamino)-1(R)-hydroxyethyl)-8-hydroxyquinolin-2(1H)-one heminapadisylate.
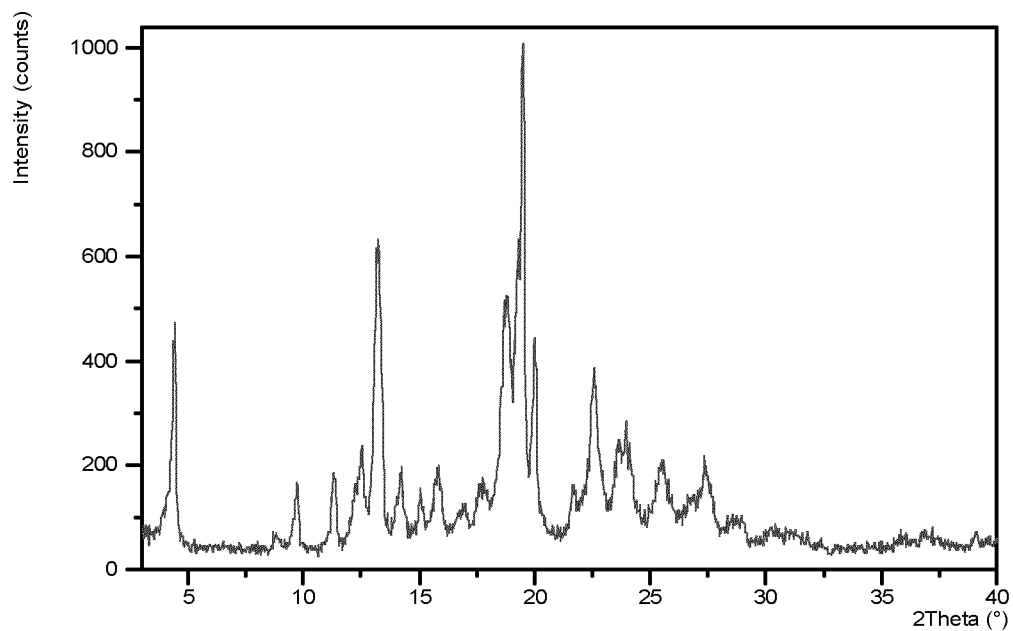

Figure 2: DSC pattern of Type β polymorph of 5-(2-(6-(2,2-Difluoro-2-phenylethoxy)hexylamino)-1(R)-hydroxyethyl)-8-hydroxyquinolin-2(1H)-one heminapadisylate of the invention.
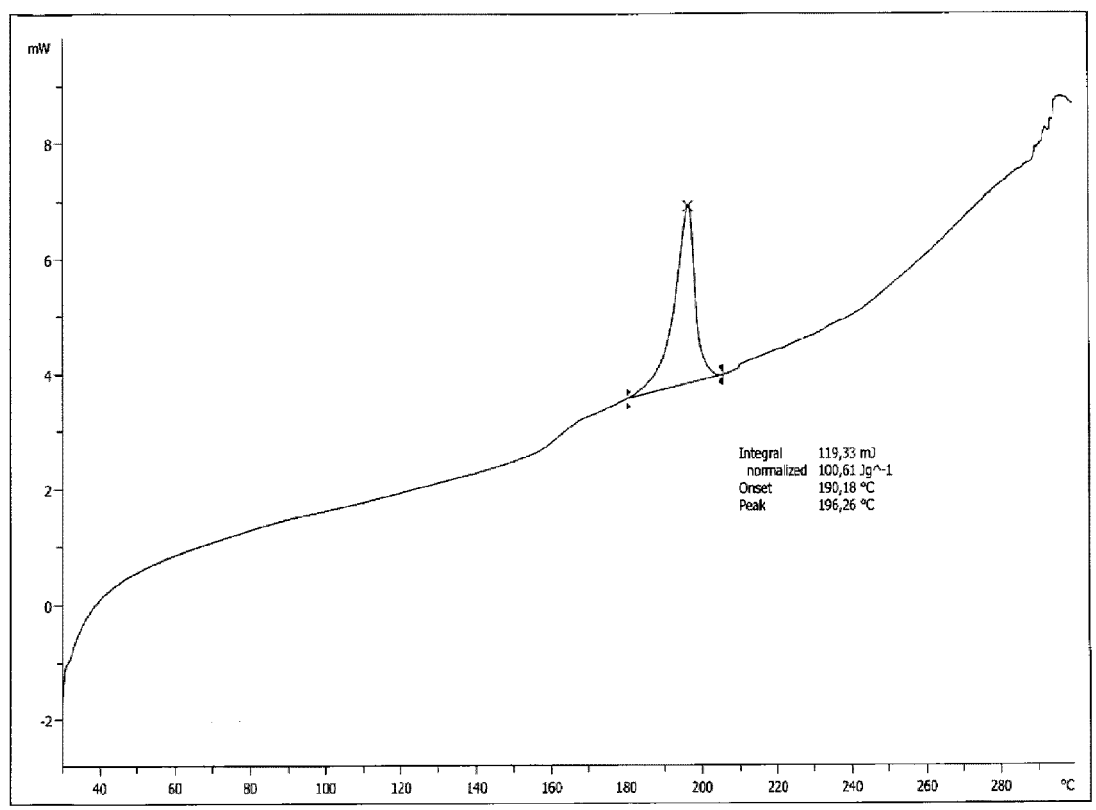

Figure 3: TGA pattern of Type β polymorph of 5-(2-(6-(2,2-Difluoro-2-phenylethoxy)hexylamino)-1(R)-hydroxyethyl)-8-hydroxyquinolin-2(1H)-one heminapadisylate of the invention.
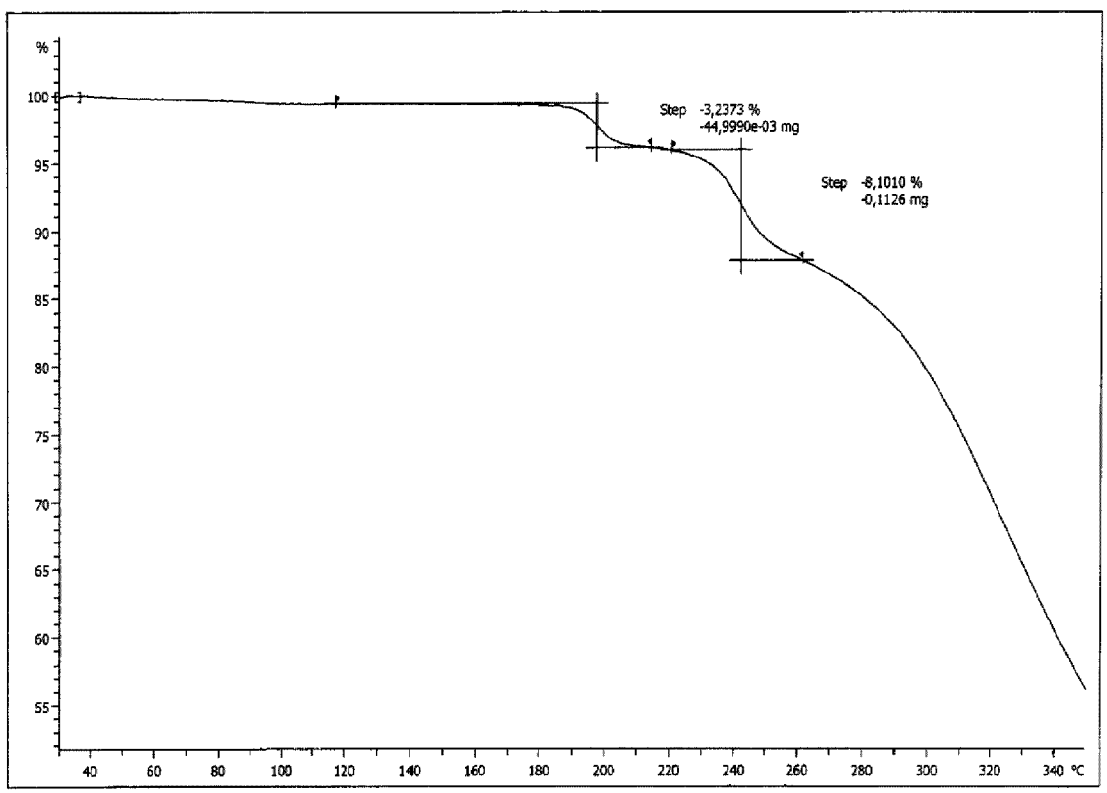

Figure 4: FT-IR pattern of Type β polymorph of 5-(2-(6-(2,2-Difluoro-2-phenylethoxy)hexylamino)-1(R)-hydroxyethyl)-8-hydroxyquinolin-2(1H)-one heminapadisylate of the invention.
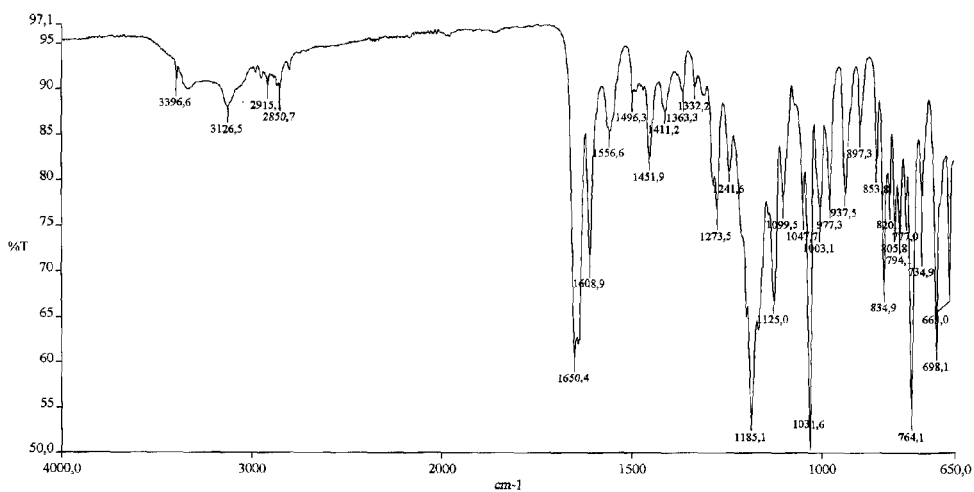

Figure 5: X-Ray Powder Diffraction (XRPD) pattern of Hydrate polymorph of 5-(2-(6-(2,2-Difluoro-2-phenylethoxy)hexylamino)-1(R)-hydroxyethyl)-8-hydroxyquinolin-2(1H)-one heminapadisylate, hemihydrate of the invention.
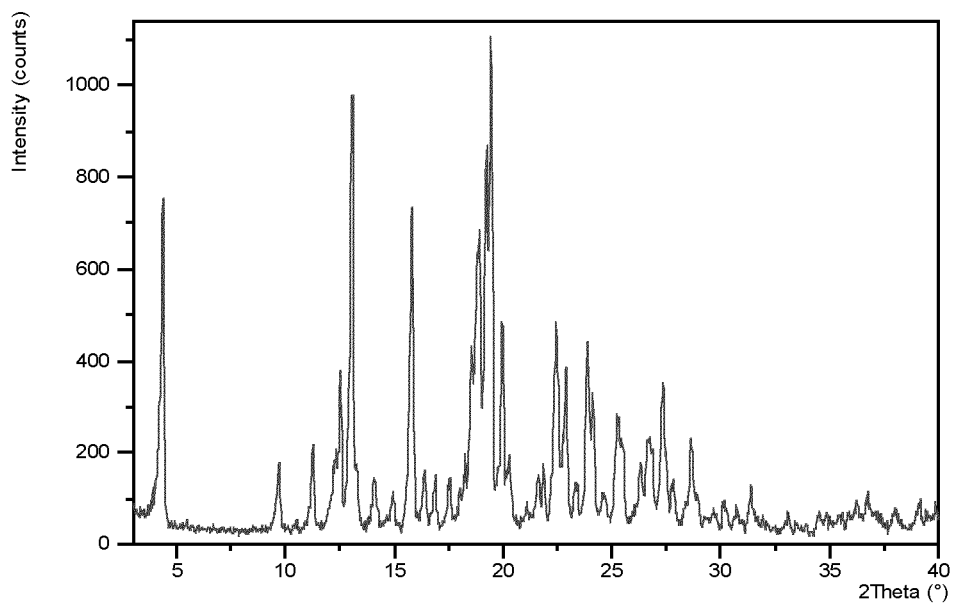

Figure 6: DSC pattern of Hydrate polymorph of 5-(2-(6-(2,2-Difluoro-2-phenylethoxy)hexylamino)-1(R)-hydroxyethyl)-8-hydroxyquinolin-2(1H)-one heminapadisylate, hemihydrate of the invention.
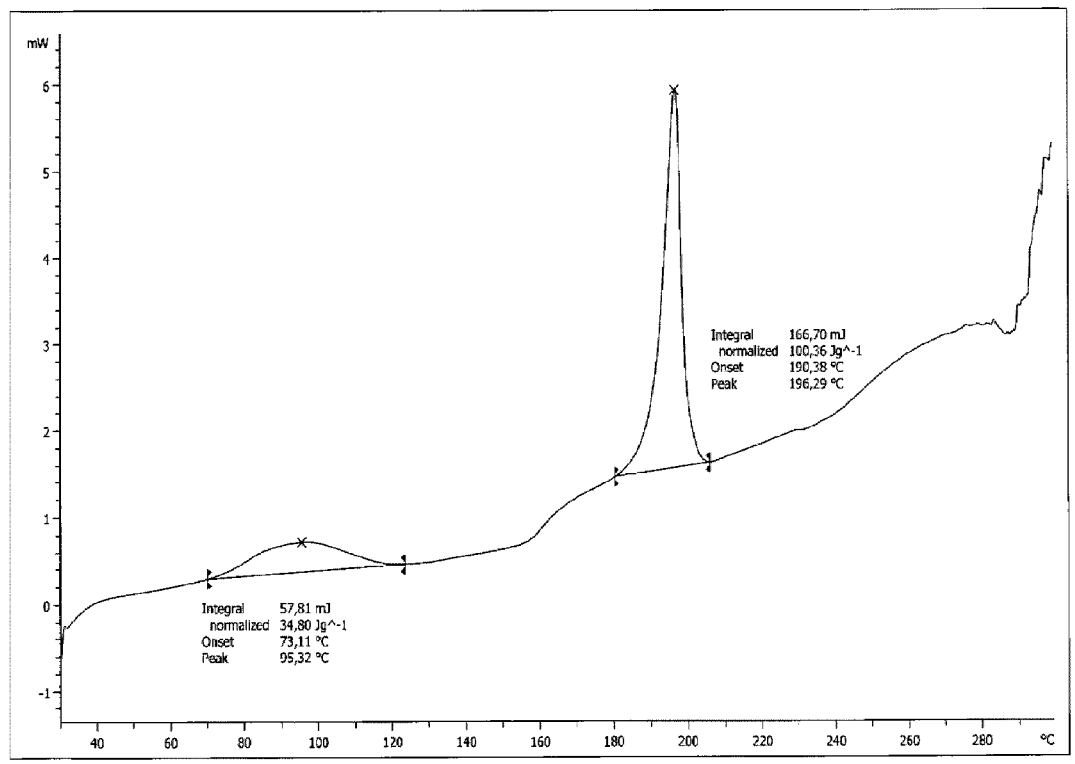

Figure 7: TGA pattern of Hydrate polymorph of 5-(2-(6-(2,2-Difluoro-2-phenylethoxy)hexylamino)-1(R)-hydroxyethyl)-8-hydroxyquinolin-2(1H)-one heminapadisylate, hemihydrate of the invention.
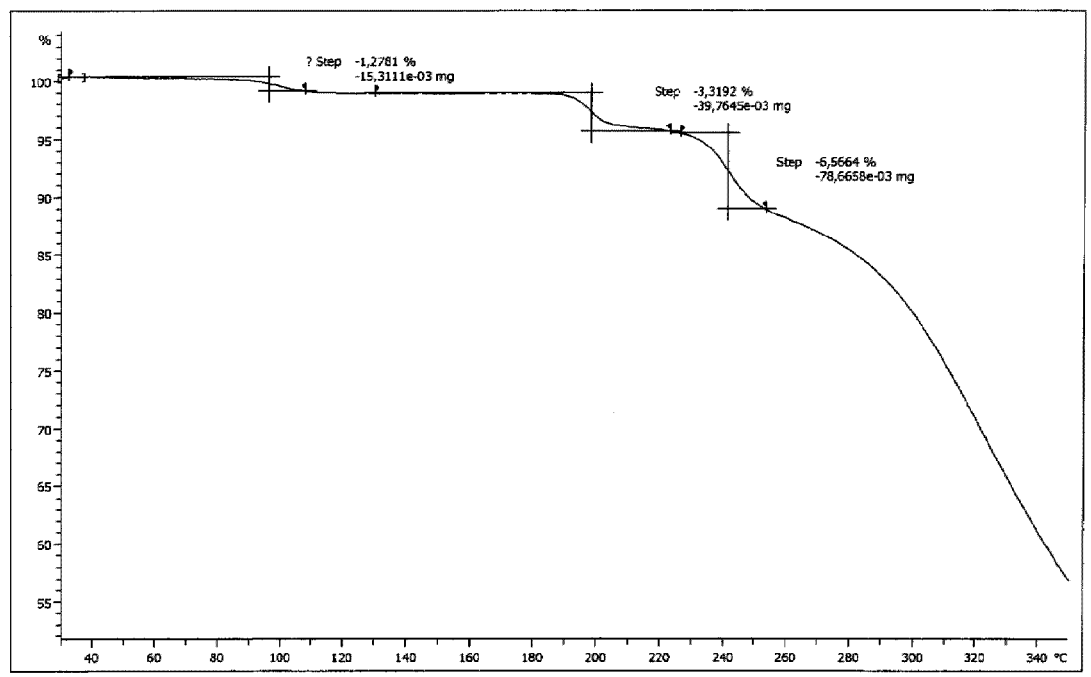

Figure 8: FT-IR pattern of Hydrate polymorph of 5-(2-(6-(2,2-Difluoro-2-phenylethoxy)hexylamino)-1(R)-hydroxyethyl)-8-hydroxyquinolin-2(1H)-one heminapadisylate, hemihydrate of the invention.
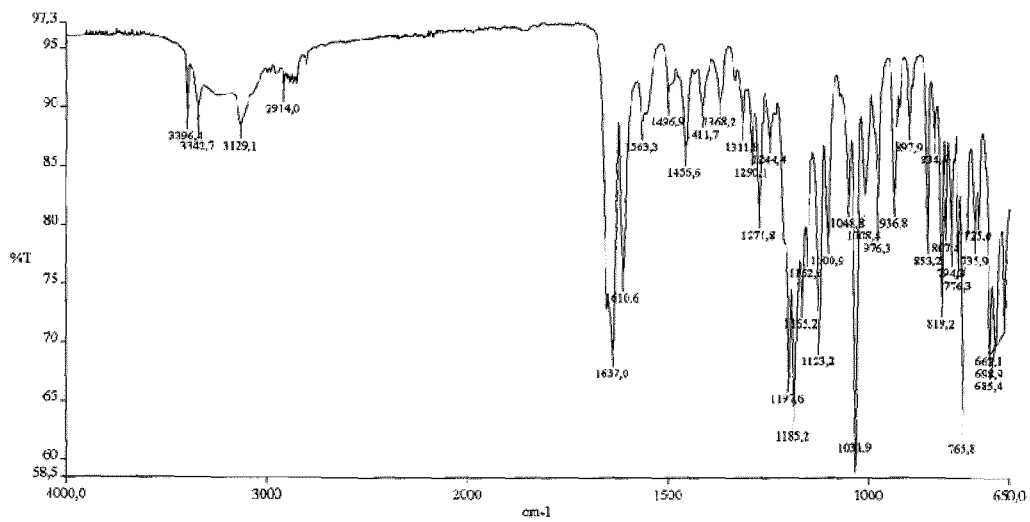

Figure 9: X-Ray Powder Diffraction (XRPD) pattern of samples of the alpha, beta and Hydrate polymorphs of 5-(2-(6-(2,2-Difluoro-2-phenylethoxy)hexylamino)-1(R)-hydroxyethyl)-8-hydroxyquinolin-2(1H)-one heminapadisylate.
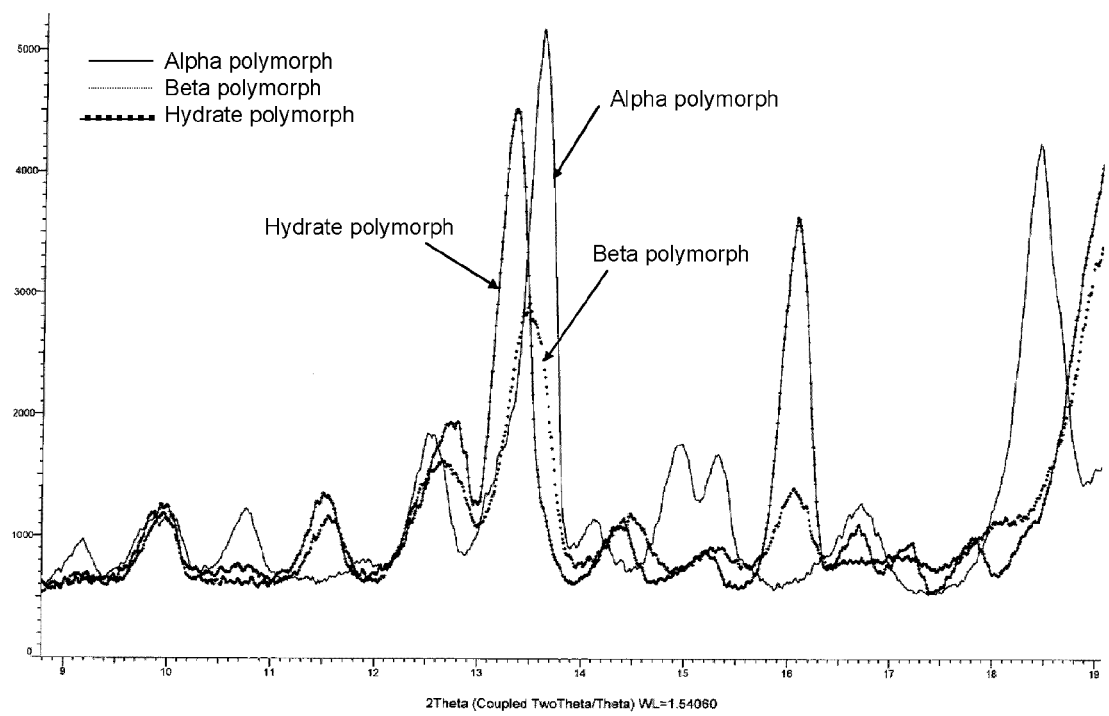

POLYMORPHIC CRYSTAL FORMS OF 5-(2-{[6-(2,2-DIFLUORO-2-PHENYLETHOXY)HEXYL]AMINO}-1-(R)-HYDROXYETHYL)-8-HYDROXYQUINOLIN-2(1H)-ONE, HEMINAPADISYTLATE AS AGONIST OF THE β2 ADRENERGIC RECEPTOR

This application is a national stage filing under 35 U.S.C. §371 of International Application No. PCT/EP2013/055488, filed on Mar. 15, 2013, which claims priority of European Patent Application No. 12382101.9, filed on Mar. 20, 2012, and U.S. Provisional Patent Application No. 61/622,266, filed on Apr. 10, 2012. The contents of all listed applications are incorporated herein by reference.

FIELD OF THE INVENTION

The present invention is directed to novel polymorphic crystal forms of a 5-(2-{[6-(2,2-difluoro-2-phenylethoxy)hexyl]amino}-1-(R)-hydroxyethyl)-8-hydroxyquinolin-2(1H)-one, heminapadisylate. The invention is also directed to pharmaceutical compositions comprising said polymorphic crystal forms, methods of using them to treat respiratory diseases associated with β2 adrenergic receptor activity and a process for preparing such polymorphic crystal forms.

BACKGROUND OF THE INVENTION 5-(2-{[6-(2,2-difluoro-2-phenylethoxy)hexyl]amino}-1-(R)-hydroxyethyl)-8-hydroxyquinolin-2(1H)-one (Compound I) is a potent β2 adrenoceptor agonist first disclosed in WO 2006/122788. This compound has the following chemical formula.

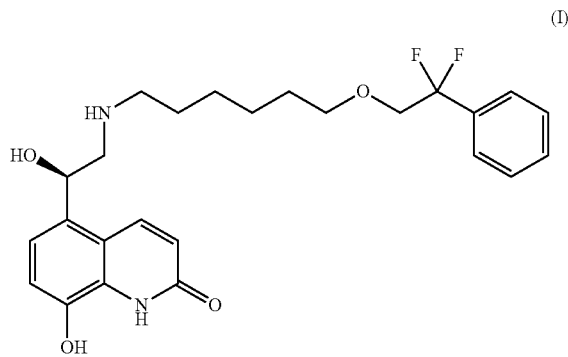 [SMILES: O=c1ccc2c([C@@H](O)CNCCCCCCOCC(F)(F)c3ccccc3)ccc(O)c2[nH]1]

(I)

Crystalline naphthalene-1,5-disulfonic acid salts (heminapadisylates) of 5-(2-{[6-(2,2-difluoro-2-phenylethoxy)hexyl]amino}-1(R)-hydroxyethyl)-8-hydroxyquinolin-2 (1H)-one have been described in WO 2008/095720. The crystalline heminapadisylate salt of compound (I) (hereinafter, called type α polymorph) is identified by the X-Ray Powder Diffraction, DSC pattern and TGA pattern. This compound has the following chemical formula.

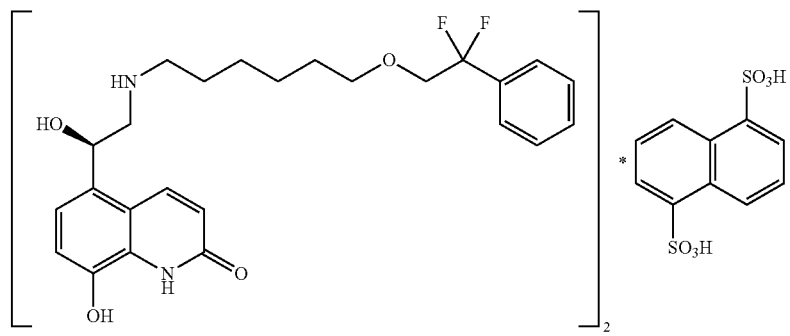

WO 2010/102831 describes an improved process for preparing the heminapadisylate salt of compound of formula (I). In particular the heminapadisylate salt is obtained in a one pot reaction without isolating said compound of formula (I). Once the hydrogenation process of 8-(benzyloxy)-5-((1R)-2-{[6-(2,2-difluoro-2-phenylethoxy)-hexyl]amino}-1-hydroxyethyl)quinolin-2(1H)-one is completed and the catalyst is removed from the reaction mixture, a solution of naphthalene-1,5-disulfonic acid tetrahydrate in methanol/acetic acid (2:1) is added to the reaction mixture. This process results in formation of the type α polymorph previously disclosed in WO 2008/095720.

This compound as a potent β2 adrenergic receptor agonists is advantageously administered directly into the respiratory tract by inhalation when used for treating pulmonary or respiratory disorders. Several types of pharmaceutical inhalation devices have been developed for administering therapeutic agents by inhalation including dry powder inhalers (DPI), metered-dose inhalers (MDI) and nebulizer inhalers.

Dry powder inhalers are well known devices for administering pharmaceutically active agents to the respiratory tract. They are particularly suitable when used for the administration of active agents in the treatment of respiratory diseases such as asthma, COPD, emphysema or the like. Since the drug acts directly on the target organ, smaller quantities of the active ingredient should be used.

Dry powder formulations typically comprise a pharmaceutically active agent and an excess of a pharmaceutically acceptable excipient or carrier. The efficacy of a dry powder inhaler is related to the extent of the drug deposition in the lungs, which in turn depends on the drug formulation and the device being used. In order to be able to reach the lower respiratory airways, the drug needs to be delivered in finely divided particles, with an aerodynamic diameter of less than 5 μm.

The Fine Particle Dose (FPD) of a drug from a dry powder inhaler is a measure of the quantity of drug of effectively deliverable particle size (i.e. with an aerodynamic diameter no greater than 5 μm) emitted after a single actuation of the DPI. The Fine Particle Fraction (FPF) is the percentage (%) of the emitted dose that the FPD represents. A high FPF is clearly desirable as more of the administered drug will be able to reach the lungs where it can be effective and thus less amount of drug will be required to achieve the optimum dose of the drug.

The use of an additive material to improve the Fine Particle Fraction (FPF) has been extensively used in a dry powder formulation. It was first mentioned in a PCT application No. WO 87/05213 where the preparation of an excipient (lactose) containing a lubricant, such as magnesium stearate or sodium benzoate, was described.

WO 96/23485 describes the preparation of a dry powder formulation containing additive materials selected from amino acids, phospholipids or surfactants in order to promote the release of the small particles of active ingredient leading to an increase in the Fine Particle Fraction (FPF).

U.S. Pat. No. 6,645,466 describes the use of magnesium stearate in dry powder formulations for inhalation with the purpose of improving the dry powder formulation stability with regard to moisture and thereby maintaining the FPF when the formulation is tested at higher relative humidity.

WO 2005/041922 describes the use of a physiologically acceptable metal phosphate salt, such as dibasic calcium phosphate, instead of magnesium stearate, in dry powder formulations thus improving the FPF.

WO 2009/061273 describes dry powder formulations containing certain ascorbic acid derivatives. It is stated that the presence of this additive material shows good inhalation performance by increasing the FPF.

Although the problem to increase the FPF is apparently solved by means of addition of certain additive materials to the formulation, it is well known in the art that adding further ingredients to a pharmaceutical formulation leads to a greater complexity in terms of manufacturing process. For instance, some mixing problems have been described for ternary mixtures, such as agglomeration, segregation or drug uniformity issues, especially when a fine excipient is added to the drug, due to a lower adhesion to the surface of the coarse carrier particles. Moreover, additional development studies may be required in order to achieve the regulatory approval of a new ingredient for inhalation administration.

It has been surprisingly found that new polymorphic crystal forms of the heminapadisylate salt of compound I exhibit a higher Fine Particle Fraction (FPF) than the standard Type α polymorph, while maintaining the crystallinity, non hygroscopicity and stability properties. The good inhalation performance of the new polymorphic crystal forms in a dry powder formulation is enhanced without the presence of any further additive material.

SUMMARY OF THE INVENTION

The present invention is related to novel polymorphic crystal forms of the heminapadisylate salt of 5-(2-{[6-(2,2-difluoro-2-phenylethoxy)hexyl]amino}-1-(R)-hydroxyethyl)-8-hydroxyquinolin-2(1H)-one (Compound I) and a process for their preparation.

In particular, the present invention is related to two polymorphic crystal forms of the heminapadisylate of Compound (I), namely an anhydrate form (hereinafter, called type β polymorph) and a hemihydrate form (hereinafter, called hydrate polymorph).

Thus, the present invention provides a crystalline polymorph of 5-(2-{[6-(2,2-difluoro-2-phenylethoxy)hexyl]amino}-1-(R)-hydroxyethyl)-8-hydroxyquinolin-2(1H)-one heminapadisylate, which is (i) a hydrate polymorph, or (ii) or a type β polymorph which is obtainable by drying said hydrate polymorph, wherein:

the hydrate polymorph has:
  a) an X-Ray Powder Diffraction (XRPD) pattern with peaks at 13.3, 16.1 and 19.2 and degrees 2θ (±0.1 degrees 2θ); and/or
  b) a Differential Scanning Calorimetery (DSC) trace which shows a first endotherm in the range 75-120° C. (±5° C.) and a second endotherm with an onset at 190° C. (±1° C.), and the type β polymorph has:
  a) an X-Ray Powder Diffraction (XRPD) pattern with a peak at 19.1 degrees 2θ (±0.1 degrees 2θ); and/or
  b) a Differential Scanning Calorimetery (DSC) trace which shows an endotherm with an onset at 190° C. (±1° C.).

The invention also provides a pharmaceutical composition comprising the polymorph salt of the invention and a pharmaceutically-acceptable carrier. The invention further provides combinations comprising the polymorph salt of the invention and one or more other therapeutic agents and pharmaceutical compositions comprising such combinations.

The invention also provides a method of treating a pulmonary disease or condition associated with β2 adrenergic receptor activity such as asthma or chronic obstructive pulmonary disease, in a mammal, comprising administering to the mammal, a therapeutically effective amount of a polymorph salt of the invention. The invention further provides a method of treatment comprising administering a therapeutically effective amount of a combination of a polymorph salt of the invention together with one or more other therapeutic agents.

The invention further provides a method for preparing a polymorph salt of the invention which is suitable on an industrial scale.

The invention also provides a polymorph salt of the invention as described herein for use in medical therapy, as well as the use of a polymorph salt of the invention in the manufacture of a formulation or medicament for treating a pulmonary disease or condition associated with β2 adrenergic receptor activity such as asthma or chronic obstructive pulmonary disease in a mammal.

BRIEF DESCRIPTION OF FIGURES

FIG. 1 shows the X-Ray Powder Diffraction (XRPD) pattern of Type β polymorph of 5-(2-(6-(2,2-Difluoro-2-phenylethoxy)hexylamino)-1(R)-hydroxyethyl)-8-hydroxyquinolin-2(1H)-one heminapadisylate of the invention. Y axis presents intensity (counts). X axis show 2 Theta (°).

FIG. 2 shows the DSC pattern of Type β polymorph of 5-(2-(6-(2,2-Difluoro-2-phenylethoxy) hexylamino)-1(R)-hydroxyethyl)-8-hydroxyquinolin-2(1H)-one heminapadisylate of the invention. Y axis presents energy (W). X axis is temperature (° C.).

FIG. 3 shows the TGA pattern of Type β polymorph of 5-(2-(6-(2,2-Difluoro-2-phenylethoxy)hexylamino)-1(R)-hydroxyethyl)-8-hydroxyquinolin-2(1H)-one heminapadisylate of the invention. Y axis represents weight (%). X axis is temperature (° C.).

FIG. 4 shows the FT-IR pattern of Type β polymorph of 5-(2-(6-(2,2-Difluoro-2-phenylethoxy)hexylamino)-1(R)-hydroxyethyl)-8-hydroxyquinolin-2(1H)-one heminapadisylate of the invention. Y axis is Transmittance (%). X axis is wavenumber ($cm^{-1}$).

FIG. 5 shows the X-Ray Powder Diffraction (XRPD) pattern of Hydrate polymorph of 5-(2-(6-(2,2-Difluoro-2-phenylethoxy)hexylamino)-1(R)-hydroxyethyl)-8-hydroxyquinolin-2(1H)-one heminapadisylate, hemihydrate of the invention. Y axis is intensity (counts). X axis show 2 Theta (°).

FIG. 6 shows the DSC pattern of Hydrate polymorph of 5-(2-(6-(2,2-Difluoro-2-phenylethoxy)hexylamino)-1(R)-hydroxyethyl)-8-hydroxyquinolin-2(1H)-one heminapadisylate, hemihydrate of the invention. Y axis represents energy (W). X axis are temperature (° C.).

FIG. 7 shows the TGA pattern of Hydrate polymorph of 5-(2-(6-(2,2-Difluoro-2-phenylethoxy)hexylamino)-1(R)-hydroxyethyl)-8-hydroxyquinolin-2(1H)-one heminapadisylate, hemihydrate of the invention. Y axis are weight (%). X axis are temperature (° C.).

FIG. 8 shows the FT-IR pattern of Hydrate polymorph of 5-(2-(6-(2,2-Difluoro-2-phenylethoxy)hexylamino)-1(R)-hydroxyethyl)-8-hydroxyquinolin-2(1H)-one heminapadisylate, hemihydrate of the invention. Y axis are Transmittance (%). X axis are wavenumber ($cm^{-1}$).

FIG. 9 shows the X-Ray Powder Diffraction (XRPD) pattern of samples of the Type α, Type β and Hydrate polymorphs of 5-(2-(6-(2,2-Difluoro-2-phenylethoxy)hexylamino)-1(R)-hydroxyethyl)-8-hydroxyquinolin-2(1H)-one heminapadisylate. Y axis are intensity (counts). X axis show 2 Theta (°).

DETAILED DESCRIPTION OF THE INVENTION

When describing the salts, compositions and methods of the invention, the following terms have the following meanings, unless otherwise indicated.

The term "polymorphism" refers to the ability of a compound to crystallize into more than one distinct crystal species. Polymorphs have an identical chemical structure but often quite different physicochemical properties, polymorphs include enantiotropic polymorphs and monotropic polymorphs.

The term "amorphous" refers to a disordered solid state, which may appear during manufacture of the drug substance (crystallization step, drying, and milling) or the drug product (granulation, compression). The X-ray powder diffraction pattern of an amorphous solid exhibits no sharp peaks.

The term "therapeutically effective amount" refers to an amount sufficient to effect treatment when administered to a patient in need of treatment.

The term "treatment" as used herein refers to the treatment of a disease or medical condition in a human patient which includes:

(a) preventing the disease or medical condition from occurring, i.e., prophylactic treatment of a patient;

(b) ameliorating the disease or medical condition, i.e., causing regression of the disease or medical condition in a patient;

(c) suppressing the disease or medical condition, i.e., slowing the development of the disease or medical condition in a patient; or (d) alleviating the symptoms of the disease or medical condition in a patient.

The phrase "pulmonary disease or condition associated with β2 adrenergic receptor activity" includes all pulmonary disease states and/or conditions that are acknowledged now, or that are found in the future, to be associated with β2 adrenergic receptor activity. Such disease states include, but are not limited to asthma and chronic obstructive pulmonary disease (including chronic bronchitis and emphysema).

The type β polymorph is typically obtainable by drying the hydrate polymorph of the invention at 105° C. for 20 hours, preferably in a vacuum.

The type β polymorph of the invention typically has an X-ray powder diffraction (XRPD) pattern with one or more additional peaks at 13.5, 19.7, 20.3, 22.8, 23.8 and 24.2 degrees 2θ (±0.1 degrees 2θ). Preferably two or more such peaks are observed, more preferably three or more, more preferably four.

The type β polymorph of the invention preferably has an X-ray powder diffraction (XRPD) pattern with one or more additional peaks at 10.0, 11.6, 12.7, 13.5, 14.5, 16.1, 19.7, 20.3, 22.0, 22.8, 23.8, 24.2. 25.8, 27.1, 27.7, 29.2 and 39.4 degrees 2θ (±0.1 degrees 2θ). Preferably two or more such peaks are observed, more preferably three or more, more preferably four or more, more preferably five or more, more preferably ten or more. Most preferably all such peaks are observed.

Thus, it is particularly preferred that the type β polymorph of the invention has an X-ray powder diffraction (XRPD) pattern with peaks at 10.0, 11.6, 12.7, 13.5, 14.5, 16.1, 19.1, 19.7, 20.3, 22.0, 22.8, 23.8, 24.2. 25.8, 27.1, 27.7, 29.2 and 39.4 degrees 2θ (±0.1 degrees 2θ).

It is also particularly preferred that the type β polymorph of the invention has an X-ray powder diffraction (XRPD) pattern with peaks at 11.6, 14.5, 16.1, 19.1, 20.3, 22.0, 24.2. 27.1 and 29.2 degrees 2θ (±0.1 degrees 2θ).

Typically, the peak at 19.7 degrees 2θ (±0.1 degrees 2θ) is most intense for the type β polymorph. Preferably, the peak at 19.7 degrees 2θ (±0.1 degrees 2θ) is at least 25% more intense than the next most intense peak.

Preferably, the type β polymorph has a peak at 13.5 degrees 2θ (±0.1 degrees 2θ). Preferably, the type β polymorph has does not have a peak at 13.6 degrees 2θ (±0.1 degrees 2θ). More preferably the type β polymorph has a peak at 13.5 degrees 2θ (±0.1 degrees 2θ) and does not have a peak at 13.6 degrees 2θ (±0.1 degrees 2θ).

The type β polymorph of the invention typically has a Differential Scanning Calorimetery (DSC) trace with an endotherm with an onset at 190° C. (±1° C.). The endotherm is a sharp endotherm. Preferably, the endotherm has an onset at 190° C. (±0.5° C.), more preferably at 190.2° C. (±0.1° C.). Typically, the endotherm has a peak at 196° C. (±1° C.). Preferably, the peak is at 196° C. (±0.5° C.), more preferably at 196.3° C. (±0.1° C.).

The type β polymorph of the invention typically has an infrared spectrum with absorption bands at 1650, 1185, 1031, and 764 $cm^{-1}$ (±1 $cm^{-1}$).

The type β polymorph of the invention preferably has an infra red spectrum with one or more additional absorption bands 1451, 1273, 834 and 698 $cm^{-1}$ (±1 $cm^{-1}$). Preferably two or more such peaks are observed, more preferably three or more. Most preferably all such peaks are observed.

The type β polymorph of the invention more preferably has an infra red spectrum with one or more additional absorption bands at 3396, 3126, 2915, 2850, 1608, 1556, 1496, 1451, 1411, 1363, 1332, 1273, 1241, 1125, 1099, 1047, 1003, 977, 937, 897, 853, 834, 820, 805, 794, 777, 734, 698 and 663 $cm^{-1}$ (±1 $cm^{-1}$). Preferably five or more such peaks are observed, more preferably ten or more, more preferably fifteen or more, more preferably twenty or more, more preferably twenty five or more. Most preferably all such peaks are observed.

Thus, it is particularly preferred that the type β polymorph of the invention has an infra red spectrum with absorption bands at 3396, 3126, 2915, 2850, 1650, 1608, 1556, 1496, 1451, 1411, 1363, 1332, 1273, 1241, 1185, 1125, 1099, 1047, 1031, 1003, 977, 937, 897, 853, 834, 820, 805, 794, 777, 764, 734, 698 and 663 $cm^{-1}$ (±1 $cm^{-1}$).

Most preferably, the type β polymorph provides:
a) an X-ray powder diffraction (XRPD) pattern substantially in accordance with FIG. 1, and/or
b) a DSC pattern substantially in accordance with FIG. 2, and/or
c) an infra red spectrum substantially in accordance with FIG. 4.

The hydrate polymorph is a hemihydrate.

The hydrate polymorph is typically obtainable by:
a) adding a solution of naphthalene-1,5-disulfonic acid tetrahydrate in methanol/acetic acid (1:1) to a solution of 5-(2-{[6-(2,2-difluoro-2-phenylethoxy)hexyl]amino}-1(R)-hydroxyethyl)-8-hydroxyquinolin-2(1H)-one in methanol/acetic acid (1:1),
b) stirring the reaction mixture at reflux for 30 minutes and leaving the reaction mixture to cool down to 20-25° C., then stirring at room temperature, preferably 20-25° C., for 20 hours,
c) isolating, filtrating and washed with methanol and drying, preferably in vacuum, at 50° C.

The hydrate polymorph typically has a X-ray powder diffraction (XRPD) pattern with one or more additional peaks at 12.7, 19.6, 20.2, 22.7, 23.1, 24.2 and 27.7 degrees 2θ (±0.1 degrees 2θ). Preferably two or more such peaks are observed, more preferably three or more, more preferably four or more. Most preferably all such peaks are observed.

The hydrate polymorph preferably has a X-ray powder diffraction (XRPD) pattern with one or more additional peaks at 9.9, 11.5, 12.7, 14.4, 15.2, 19.6, 20.2, 21.9, 22.7, 23.1, 24.2, 25.6, 26.98, 27.6, 28.9, 30.5, 31.7, 33.4 and 37.0 degrees 2θ (±0.1 degrees 2θ). Preferably two or more such peaks are observed, more preferably three or more, more preferably four or more, more preferably five or more, more preferably ten or more, more preferably fifteen or more. Most preferably all such peaks are observed.

Thus, it is particularly preferred that the hydrate polymorph has a X-ray powder diffraction (XRPD) pattern with peaks at 9.9, 11.5, 12.7, 13.3, 14.4, 15.2, 16.1, 16.7, 19.2, 19.6, 20.2, 21.9, 22.7, 23.1, 24.2, 25.6, 27.0, 27.6, 28.9, 30.5, 31.7, 33.4 and 37.0 degrees 2θ (±0.1 degrees 2θ).

It is also particularly preferred that the hydrate polymorph has a X-ray powder diffraction (XRPD) pattern with peaks at 11.5, 13.3, 14.4, 16.1, 16.7, 19.2, 20.2, 21.9, 23.1, 24.2, 25.6, 27.0, 28.9, 30.5, 31.7, 33.4 and 37.0 degrees 2θ (±0.1 degrees 2θ).

Typically, the peak at 19.6 degrees 2θ (±0.1 degrees 2θ) is most intense for the hydrate polymorph. Preferably, the peak at 19.6 degrees 2θ (±0.1 degrees 2θ) is at least 10% more intense than the next most intense peak.

Preferably, the hydrate polymorph has peak at 13.4 degrees 2θ (±0.1 degrees 2θ). Preferably, the hydrate polymorph does not have a peak at 13.6 degrees 2θ (±0.1 degrees 2θ). More preferably, the hydrate polymorph has peak at 13.4 degrees 2θ (±0.1 degrees 2θ) and does not have a peak at 13.6 degrees 2θ (±0.1 degrees 2θ).

The hydrate polymorph typically has a Differential Scanning Calorimetery (DSC) trace which shows a first endotherm in the range 75-120° C. (±5° C.) and a second endotherm with an onset at 190° C. (±1° C.).

The first endotherm of the hydrate polymorph is a wide endotherm. It preferably has an onset at 73° C. (±1° C.). The first endotherm preferably has a peak at 95° C. (±1° C.).

The second endotherm of the hydrate polymorph is a sharp endotherm. Preferably, the second endotherm has an onset at 190° C. (±0.5° C.), more preferably at 190.4° C. (±0.1° C.). Typically, the endotherm has a peak at 196° C. (±1° C.). Preferably, the peak is at 196° C. (±0.5° C.), more preferably at 196.3° C. (±0.1° C.).

The hydrate polymorph of the invention typically has an infra red spectrum with absorption bands 1637, 1185, 1030, and 776 cm$^{-1}$ (±1 cm$^{-1}$).

The hydrate polymorph of the invention preferably has an infra red spectrum one or more additional absorption bands at 1456, 1271 and 819 cm$^{-1}$ (±1 cm$^{-1}$). Preferably two or more such peaks are observed. More preferably all such peaks are observed.

The hydrate polymorph of the invention more preferably has an infra red spectrum with one or more additional absorption bands at 3396, 3342, 3129, 2914, 1610, 1563, 1496, 1456, 1411, 1368, 1311, 1290, 1271, 1244, 1192, 1155, 1152, 1123, 1100, 1048, 1008, 976, 936, 897, 853, 819, 807, 794, 735, 725, 691, 685 and 662 cm$^{-1}$. (±1 cm$^{-1}$). Preferably five or more such peaks are observed, more preferably ten or more, more preferably fifteen or more, more preferably twenty or more, more preferably twenty five or more. Most preferably all such peaks are observed.

Thus, it is particularly preferred that the hydrate polymorph of the invention has an infra red spectrum with absorption bands at 3396, 3342, 3129, 2914, 1637, 1610, 1563, 1496, 1456, 1411, 1368, 1311, 1290, 1271, 1244, 1192, 1185, 1155, 1152, 1123, 1100, 1048, 1030, 1008, 976, 936, 897, 853, 819, 807, 794, 776, 735, 725, 691, 685 and 662 cm$^{-1}$ (±1 cm$^{-1}$).

Most preferably, the hydrate polymorph provides:
a) an X-ray powder diffraction (XRPD) pattern substantially in accordance with FIG. 5, and/or
b) a DSC pattern substantially in accordance with FIG. 6, and/or
c) an infra red spectrum substantially in accordance with FIG. 8.

Typically, the type β polymorph starts to decompose at 200° C. (±5° C., preferably ±2° C.), as measured by thermogravimetric analysis. Typically, the hydrate polymorph starts to decompose at 200° C. (±5° C., preferably ±2° C.), as measured by thermogravimetric analysis. The start of decomposition can be identified by a reduction in weight of the sample of the polymorph, as described in the Examples. The thermogravimetric (TGA) analysis can be performed using any suitable apparatus and technique. Typically, a TGA-SDTA-851 Mettler-Toledo is used, preferably as described below in the Examples.

The X-Ray Powder Diffraction (XRPD) analysis can be performed using any suitable apparatus and technique. Typically, XRPD analysis is performed on a Brucker X-ray powder diffractometer, model D2 Phaser with a Cu X-ray source, preferably as described below in the Examples.

The differential scanning calorimetry (DSC) analysis can be performed using any suitable apparatus and technique. Typically, DSC analysis is performed using a DSC-821 Mettler-Toledo, preferably as described below in the Examples.

The infrared spectrum analysis can be performed using any suitable apparatus and technique. Typically, infrared analysis is performed using a Nicolet 710 FT-IR spectrometer, preferably as described below in the Examples.

The present invention encompasses the type β polymorph isolated in a pure form, or a substantially pure form, or admixed with other polymorphs selected from the hydrate polymorph and the known type α polymorph disclosed in WO 2008/095720. The type β polymorph is preferably isolated in a pure form, or a substantially pure form. Thus, preferably the crystalline form consists, or consists essentially of, the type β polymorph. The type α polymorph is preferably not present.

The present invention also encompasses the hydrate polymorph isolated in a pure form, or a substantially pure form, or admixed with other polymorphs selected from the type β polymorph and the known type α polymorph disclosed in WO 2008/095720. The hydrate polymorph is preferably isolated in a pure form, or a substantially pure form. Thus, preferably the crystalline form consists, or consists essentially of, the hydrate polymorph. The type α polymorph is preferably not present.

For the avoidance of doubts the term "compound I" refers to a 5-(2-{[6-(2,2-difluoro-2-phenylethoxy)hexyl]amino}-1(R)-hydroxyethyl)-8-hydroxyquinolin-2(1H)-one in a free base form and having the following chemical structure:

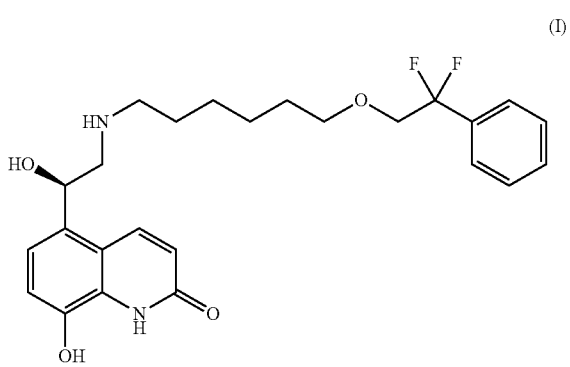 [SMILES: O=c1ccc2c([C@@H](O)CNCCCCCCOCC(F)(F)c3ccccc3)ccc(O)c2[nH]1]

(I)

The term "heminapadisylate salt of compound (I)" refers to 5-(2-{[6-(2,2-difluoro-2-phenylethoxy)hexyl]amino}-1(R)-hydroxyethyl)-8-hydroxyquinolin-2(1H)-one, heminapadisylate having the following chemical structure:

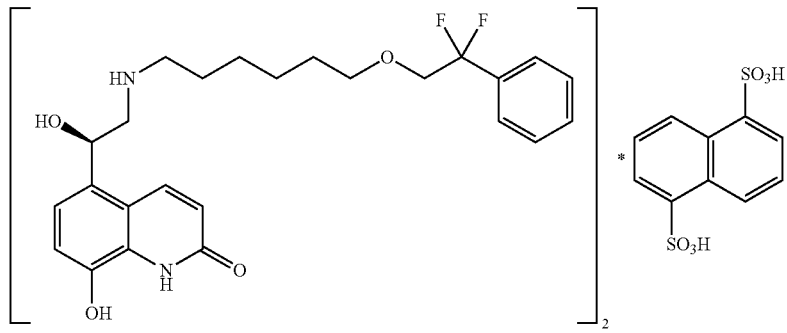

The term "crystalline Type α polymorph" or "Type α polymorph" refers to the heminapadisylate salt of compound (I) as disclosed and characterized in the published International Patent Applications No. WO 2008/095720 and WO 2010/102831.

The invention also encompasses a pharmaceutical composition comprising a therapeutically effective amount of a crystalline Type β polymorph of 5-(2-{[6-(2,2-difluoro-2-phenylethoxy)hexyl]amino}-1(R)-hydroxyethyl)-8-hydroxyquinolin-2(1H)-one, heminapadisylate, and a pharmaceutically acceptable carrier.

The invention also encompasses a pharmaceutical composition comprising a therapeutically effective amount of a crystalline Hydrate polymorph of 5-(2-{[6-(2,2-difluoro-2-phenylethoxy)hexyl]amino}-1(R)-hydroxyethyl)-8-hydroxyquinolin-2(1H)-one, heminapadisylate, hemihydrate, and a pharmaceutically acceptable carrier.

The polymorphic forms of the invention are stable and thus retain their polymorphic structure during formation or preparation of the pharmaceutical composition.

The carrier for example, a mono-, di- or polysaccharide or sugar alcohol, such as lactose, mannitol or glucose is generally employed. Preferably, the lactose used as a carrier in the present invention is a crystalline alpha lactose monohydrate. Suitable commercially available lactose materials can be used as a carrier. Examples of such lactose are purchased from DMV Internacional (Respitose GR-001, Respitose SV-001, Respitose SV-003 or a mixture thereof), Meggle (Capsulac 60, Inhalac 70, Inhalac 120, Inhalac 230, Capsulac 60 INH, Sorbolac 400, or a mixture thereof), and Borculo Domo (Lactohale 100-200, Lactohale 200-300 and Lactohale 100-300, or a mixture thereof).

In another embodiment, the carrier used may be in the form of a mixture of different types of carrier having different particles sizes. For example, a mixture of a fine carrier and a coarse carrier may be present in the formulation, wherein the average particle size of the fine carrier is lower than the average particle size of the coarse carrier. Preferably the fine carrier may have an average particle size range of 1-50 μm, preferably 2-20 μm, more preferably, 5-15 μm. The coarse carrier may have an average particle size range of 20-1000 μm, preferably 50-500 μm, more preferably 90-400 μm, being most preferably, 150-300 μm. The content of the fine carrier with respect to the coarse carrier may vary from 1% to 10%, preferably, from 3% to 6%, e.g., 5%, by weight of the total coarse carrier.

In one embodiment lactose particles for use in formulations of the invention is a mixture of a coarse lactose having a d10 of 90-160 μm, a d50 of 170-270 μm, and d90 of 290-400 μm and a fine lactose having a d10 of 2-4 μm, a d50 of 7-10 μm, and d90 of 15-24 μm.

The ratio by weight between the lactose particles and the active ingredient of the present invention, will depend on the inhaler device used, but is typically, e.g., 800:1 to 40000:1, for example 1600:1 to 20000:1, e.g., 3000-8000:1.

In a preferred embodiment, the active ingredient of the present invention is administered in the form of a dry powder formulation in admixture with lactose, in a ratio by weight of the active ingredient to lactose of 1:20000 to 1:1600, wherein the active ingredient particles have an average particle size of from 1.5 to 5 μm in diameter, e.g., less than 3 μm in diameter, and the lactose particles have a d10 of 90-160 μm, a d50 of 170-270 μm, and d90 of 290-400 μm. Said lactose particles are optionally mixed with a fine lactose having a particle size d10 of 2-4 μm, a d50 of 7-10 μm, and d90 of 15-24 μm.

Preferably, the pharmaceutical composition of the present invention is formulated for administration by inhalation. It is further preferred that the pharmaceutical composition does not contain an additive material for improving the Fine Particle Fraction (FPF). Thus, the pharmaceutical composition preferably comprises less than 5 wt % of said additive material, more preferably less than 1 wt %, more preferably less than 0.1 wt %, most preferably less than 0.01 wt %. Thus, said additive material is most preferably absent or substantially absent from the pharmaceutical composition.

Additive materials for improving the Fine Particle Fraction (FPF) are well known to those skilled in the art. Suitable additive materials are described in WO 87/05213, WO 96/23485, U.S. Pat. No. 6,645,466, WO 2005/041922 and WO 2009/061273. Thus, the additive material is typically a lubricant (for example magnesium stearate or sodium benzoate), an amino acid, a phospholipid, a surfactant, a metal phosphate (such as dibasic calcium phosphate) or an ascorbic acid derivative.

In an embodiment of the present invention the pharmaceutical composition further comprises a therapeutically effective amount of one or more other therapeutic agents. Preferably other therapeutic agents are selected from a corticosteroid, an anticholinergic agent and a PDE4 inhibitor.

The crystalline Type β and Hydrate polymorphs of the present invention as hereinabove defined may also be combined with one or more other therapeutic agents, in particular one or more drugs selected from the group consisting of corticosteroids, anticholinergic agents and PDE4 inhibitors.

The invention is also directed to a method of treating a disease or condition in a mammal associated with β2 adrenergic receptor activity, the method comprising administering to the mammal, a therapeutically effective amount of the pharmaceutical composition comprising the crystalline polymorphic form as defined according to the present invention. It is of particular relevance the method applied to the treatment of a disease or condition which is a pulmonary disease, preferably asthma or chronic obstructive pulmonary disease.

In particular, the method of treating a pulmonary disease or condition comprises administering to the mammal a therapeutically effective amount of a pharmaceutical composition according to the present invention and a therapeutically effective amount of one or more other therapeutic agents, such as a corticosteroid, an anticholinergic agent, or a PDE4 inhibitor.

The invention is also directed to the use of the crystalline Type β and/or Hydrate polymorph as defined according to the invention, in the manufacture of a medicament for the treatment of a pulmonary disease or condition in a mammal. The mammal is preferably a human being. Particularly relevant pulmonary diseases or conditions are asthma or chronic obstructive pulmonary disease.

The invention is also directed to the crystalline Type β and/or Hydrate polymorph as defined according to the invention for use in the treatment of a pulmonary disease or condition. The mammal is preferably a human being. Particularly relevant pulmonary diseases or conditions are asthma or chronic obstructive pulmonary disease.

General Synthetic Procedures

The crystalline Type β and Hydrate polymorphs of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Processes for preparing polymorphic crystal forms of the invention are provided as further embodiments of the invention and are illustrated by the procedures below.

The crystalline salts of the invention can be synthesized from 5-(2-{[6-(2,2-difluoro-2-phenylethoxy)hexyl]amino}-1(R)-hydroxyethyl)-8-hydroxyquinolin-2(1H)-one and from naphthalene-1,5-disulfonic acid (also known as Armstrong's Acid) or from its tetrahydrate. Both the naphthalene-1,5-disulfonic acid and its tetrahydrate are commercially available and can be purchased from, for example, Aldrich.

EXAMPLES

General.
Reagents, starting materials, and solvents were purchased from commercial suppliers and used as received.

Example 1

Crystalline 5-(2-{[6-(2,2-difluoro-2-phenylethoxy)hexyl]amino}-1(R)-hydroxyethyl)-8-hydroxyquinolin-2(1H)-one, heminapadisylate, hemihydrate (the crystalline Hydrate polymorph)

To a solution 13.9 g of 5-(2-{[6-(2,2-difluoro-2-phenylethoxy)hexyl]amino}-1(R)-hydroxyethyl)-8-hydroxyquinolin-2(1H)-one as a free base in 304 ml of methanol and 304 ml of acetic acid was slowly added a solution of 6.0 g of naphthalene-1,5-disulfonic acid tetrahydrate in 52 ml of methanol/acetic acid (1:1). The mixture was then stirred for 30 minutes at reflux temperature and then cooled down slowly to 20/25° C. The mixture was stirred at this temperature for 20 additional hours. The precipitate formed was isolated by filtration, washed with methanol and dried under vacuum at 50° C. (Yield 91% of the Hydrate polymorph).

Example 2

Crystalline 5-(2-{[6-(2,2-difluoro-2-phenylethoxy)hexyl]amino}-1(R)-hydroxyethyl)-8-hydroxyquinolin-2(1H)-one, heminapadisylate (the crystalline Type β polymorph)

Crystalline Hydrate polymorph as prepared in Example 1 was dried at 105° C. under vacuum during 24 hours to yield the anhydrous form Type β (yield 99.8%).

Example 3

Pharmaceutical Inhalation Composition Comprising a Polymorphic Salt of Compound (I) and a Carrier The process for manufacturing the pharmaceutical composition comprising a polymorphic salt of compound (I) (Type α, Type β or Hydrate) and a carrier is as follows:
1. 20% by weight of lactose used as a carrier was blended with one polymorph (Type α, Type β or Hydrate). The resulting mixture was sieved and mixed again.
2. The remaining 80% by weight of lactose was sieved and added to the mixture of Step 1. The whole mixture was blended, sieved and blended again resulting in the final inhalation powder blend.

When two different types of lactose, for example a coarse lactose and a fine lactose as defined above, are used, these lactose types are previously mixed together and blended before adding the polymorph salt of the invention as described above.

The test on the aerodynamic assessment of the fine particles (FPD<5 μm) of the inhalation powder composition is carried out in combination with the Genuair® inhaler. The Fine Particle Fraction of the three formulations was calculated on basis of the principles of the aerodynamic assessment of fine particles according to the Current European pharmacopoeia (Ph. Eur. Chapter 2.9.18) and USP<601> by the aid of aerodynamic impactor analyses using a modified Anderson Cascade Impactor (ACI), 60 L/min-configuration including pre-separator, stage-1, -0, and stage 1-7 (filter stage). The content of the active ingredient on each stage of the impactor is determined my means of HPLC.

The fine particle dose (FPD<5 μm) is calculated based on Ph. Eur. Chapter 2.9.18 and USP<601> by point to point interpolation per dosage. Linear point to point interpolation is done between the stages with a corresponding effective cut-off diameter which enclose the 5 μm mark.

To obtain the Fine Particle Dose, the cumulative percent value (y-value) at which the line of data plot crosses 5 μm mark is determined. The found cumulative percent must be multiplied by the sum of mass of the active ingredient per dosage on stage-1-stage 7 (Filter) to obtain the fine particle dose, <5 μm, in μg.

$$\text{FPD } [\mu g] = y_{FPD} \cdot F/100\%$$

FPD=Fine particle dose<5 μm of the active ingredient per dosage [μg].

$y_{FPD}$=y-value of cumulative percentage of mass at a particle size of 5 μm evaluated by linear point to point interpolation [%].

F=sum of mass on stage-1-stage 7 (filter) per dosage [μg].

The Fine Particle Fraction (FPF) is the percentage of the emitted dose that the Fine Particel Dose represents and is calculated as follows:

$$\text{FPF } [\%] = (\text{FPD } [\mu g]/\text{Total sum } [\mu g]) \cdot 100$$

Total sum=the amount of drug substance in the respective impactor (Adapter-Filter).

The results of the FPF are shown in the following Table 1:

TABLE 1

| Formulation | FPF (%) |
| --- | --- |
| Comparative Example (polymorph Type α as disclosed in WO 2008/095720) | 42.2 |
| Polymorph Type β | 49.3 |
| Polymorph Hydrate | 49.8 |

As it can be seen from the table, the fine particle fraction was increased by about 17% when compared with the comparative Example (α polymorph). The increase in the FPF is enhanced without the addition of any additive material. This finding results in a simpler manufacture of the dry powder formulation way and allows a higher portion of the administered drug to reach the lung. This results in that less amount of drug is required to achieve the optimum dose of the drug and therefore a better inhalation performance for use in the treatment of respiratory diseases is achieved.

Characterizing Data

The following charcterising data were generated for both polymorphic crystal form Type β and Hydrate (Example 1 and Example 2, respectively).

X-Ray Powder Diffraction (XRPD)

X-Ray Powder Diffraction (XRPD) analysis was performed on a Brucker X-ray powder diffractometer, model D2 Phaser with a Cu X-ray source. The method runs from 5 to 40 degrees 2-Theta with a 0.01 degree 2-Theta step size and a 0.4 second collection time at each step using a Lynxeye detector.

Crystalline Type β Polymorph.

The XRPD pattern of the crystalline Type β polymorph is shown in FIG. 1 and a summary of the XRPD angles and relative intensities are given in Table 2. The relative intensities are expressed by S=Strong, M=Medium, W=weak, VS=very Strong and VW=Very Weak.

TABLE 2

| Diffraction Angle (°2θ) | d value | Relative Intensity (%) |
| --- | --- | --- |
| 9.95 | 8.89 | W |
| 11.56 | 7.65 | W |
| 12.65 | 6.99 | W |
| 13.48 | 6.56 | M |
| 14.47 | 6.12 | VW |
| 16.06 | 5.51 | W |
| 19.09 | 4.65 | S |
| 19.69 | 4.51 | VS |
| 20.25 | 4.38 | M |
| 21.97 | 4.04 | VW |
| 22.82 | 3.89 | S |
| 23.83 | 3.73 | M |
| 24.23 | 3.67 | M |
| 25.77 | 3.45 | W |
| 27.05 | 3.29 | W |
| 27.67 | 3.22 | W |
| 29.17 | 3.06 | VW |
| 39.39 | 2.29 | VW |

Crystalline Hydrate Polymorph.

The XRPD pattern of the crystalline Hydrate polymorph is shown in FIG. 5 and a summary of the XRPD angles and relative intensities are given in Table 3. The relative intensities are expressed by S=Strong, M=Medium, W=weak, VS=very Strong and VW=Very Weak.

TABLE 3

| Diffraction Angle (°2θ) | d value | Relative Intensity |
| --- | --- | --- |
| 9.94 | 8.89 | W |
| 11.51 | 7.68 | W |
| 12.74 | 6.95 | M |
| 13.34 | 6.63 | S |
| 14.37 | 6.16 | VW |
| 15.20 | 5.82 | VW |
| 16.07 | 5.51 | S |
| 16.68 | 5.31 | VW |
| 19.17 | 4.63 | S |
| 19.63 | 4.52 | VS |
| 20.24 | 4.38 | M |
| 21.94 | 4.05 | W |
| 22.72 | 3.91 | M |
| 23.12 | 3.84 | M |
| 24.21 | 3.67 | M |
| 25.59 | 3.48 | W |
| 26.98 | 3.30 | W |
| 27.63 | 3.23 | M |
| 28.94 | 3.08 | W |
| 30.47 | 2.93 | VW |
| 31.67 | 2.82 | VW |
| 33.35 | 2.68 | VW |
| 36.54 | | VW |
| 37.04 | 2.42 | VW |

FIG. 9 shows the X-Ray Powder Diffraction (XRPD) pattern of samples of the Type α, Type β and Hydrate polymorphs of 5-(2-(6-(2,2-Difluoro-2-phenylethoxy)hexylamino)-1(R)-hydroxyethyl)-8-hydroxyquinolin-2(1H)-one heminapadisylate. As it can be seen from the figure all the 3 polymorphs Types can be unambiguously identified thus allowing easy differentiation between each other.

A summary of the XRPD angles and relative intensities for the Type α polymorph is given in Table 5. The relative intensities are expressed by S=Strong, M=Medium, W=weak, VS=very Strong and VW=Very Weak.

TABLE 5

| Diffraction Angle (°2θ) | d value | Relative Intensity (%) |
|---|---|---|
| 9.16 | 9.65 | W |
| 9.95 | 8.89 | W |
| 10.75 | 8.22 | W |
| 12.55 | 7.04 | M |
| 13.60 | 6.50 | S |
| 14.95 | 5.92 | M |
| 15.31 | 5.78 | M |
| 18.45 | 4.81 | S |
| 19.56 | 4.53 | VS |
| 19.91 | 4.46 | M |
| 20.55 | 4.32 | M |
| 21.47 | 4.13 | M |
| 22.72 | 3.91 | M |
| 23.85 | 3.73 | M |
| 25.86 | 3.44 | W |
| 27.81 | 3.21 | W |
| 28.26 | 3.15 | VW |
| 31.95 | 2.79 | VW |
| 39.27 | 2.29 | VW |

Differential Scanning Calorimetry (DSC)

The differential scanning calorimetry (DSC) analysis was obtained using a DSC-821 Mettler-Toledo, serial number 5117423874. Samples were weighed into an aluminium pan, an aluminium lid placed on top of the sample and compressed with a brass rod. Samples were equilibrated at 25° C. and heated at 10° C./min to 300° C. The instrument was calibrated using indium and zinc standards.

Crystalline Type β Polymorph.

FIG. 2 shows a DSC pattern of the Type β polymorph. The sample exhibits an endotherm with an onset of around 190° C. and there are no changes prior to the decomposition. This indicates that the sample does not convert into any other polymorphs.

Crystalline Form Hydrate Polymorph.

FIG. 5 shows a DSC pattern of the Hydrate polymorph. The sample exhibits a wide endotherm in the range 75-120° C. due to the loss of water. The second endotherm with an onset of around 190° C. corresponds to decomposition.

Thermogravimetric Analysis.

The thermogravimetric (TGA) analysis was obtained using a TGA-SDTA-851 Mettler-Toledo, serial number 5118408555. Samples were placed into a tared aluminium pan and then positioned on a platinum crucible. Samples were heated from 30° C. at 10° C./min to 350° C. The instrument was calibrated using indium and aluminium standards.

Crystalline Form Type β Polymorph.

FIG. 3 shows a TGA pattern of the Type β polymorph. The sample does not exhibit weight losses prior to the decomposition at approximately 200° C.

Crystalline Form Hydrate Polymorph.

FIG. 6 shows a TGA pattern of the Hydrate polymorph. The sample exhibits a weight loss of about 1.3% at 100° C. due to the dehydration (which corresponds to ½ water molecule). Finally the sample starts to lose weight near 200° C. due to decomposition.

Infrared Spectrum

The infrared spectrum was obtained using a Nicolet 710 FT-IR spectrometer at 2 cm$^{-1}$. Data were digitised at 1 cm$^{-1}$.

Crystalline Form Type β Polymorph.

FIG. 4 shows an IR spectrum of the Type β polymorph. The peak positions are as follows: 3396, 3126, 2915, 2850, 1650, 1608, 1556, 1496, 1451, 1411, 1363, 1332, 1273, 1241, 1185, 1125, 1099, 1047, 1031, 1003, 977, 937, 897, 853, 834, 820, 805, 794, 777, 764, 734, 698 and 663 cm$^{-1}$.

Crystalline Form Hydrate Polymorph.

FIG. 8 shows an IR spectrum of the Hydrate polymorph. The peak positions are as follows: 3396, 3342, 3129, 2914, 1637, 1610, 1563, 1496, 1456, 1411, 1368, 1311, 1290, 1271, 1244, 1192, 1185, 1155, 1152, 1123, 1100, 1048, 1030, 1008, 976, 936, 897, 853, 819, 807, 794, 776, 735, 725, 691, 685 and 662 cm$^{-1}$.

Pharmaceutical Compositions

Pharmaceutical compositions according to the present invention comprise a therapeutically effective amount of a Type β polymorph, in a pure form or admixed with Hydrate and/or Type α polymorphs and a pharmaceutically acceptable carrier.

Pharmaceutical compositions according to the present invention comprise a therapeutically effective amount of a Hydrate polymorph, in a pure form or admixed with Type β and/or Type α polymorphs and a pharmaceutically acceptable carrier.

The pharmaceutical formulations may conveniently be presented in unit dosage form and may be prepared by any of the methods well known in the art of pharmacy. All methods include the step of bringing the active ingredient(s) into association with the carrier. In general the formulations are prepared by uniformly and intimately bringing into association the active ingredient with liquid carriers or solid carriers or both and then, if necessary, shaping the product into the desired formulation.

Dry powder compositions for topical delivery to the lung by inhalation may, for example, be presented in capsules and cartridges of, for example, gelatine or blisters of, for example, laminated aluminium foil, for use in an inhaler or insufflator. Formulations generally contain a powder mix for inhalation of the polymorph of the invention and a suitable powder base (carrier substance) such as lactose or starch. Use of lactose is preferred.

Each capsule or cartridge may generally contain between 1 µg and 150 µg of each therapeutically active ingredient. Alternatively, the active ingredient (s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e.g. Nielsen et al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (Ex. EP0069715) or disks (Ex. GB 2041763; EP 0424790; DE 4239402 and EP 0674533), rotatable cylinders (Ex. EP 0166294; GB 2165159 and WO 92/09322) and rotatable frustums (Ex. WO 92/00771), all having cavities which have to be filled with powder from the container. Other multi dose devices have measuring slides (Ex. U.S. Pat. No. 5,201,308 and WO 97/00703) or measuring plungers with a local or circumferential recess to displace a certain volume of powder from the container to a delivery chamber or an air conduit (Ex. EP 0505321, WO 92/04068 and WO 92/04928), or measuring slides such as the Genuair® (formerly known as Novolizer SD2FL), which is described the following patent applications Nos: WO97/000703, WO03/000325 and WO2006/008027.

Reproducible dose measuring is one of the major concerns for multi dose inhaler devices. The powder formulation has to exhibit good and stable flow properties, because filling of the dose measuring cups or cavities is mostly under the influence of the force of gravity. For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (e.g. WO 97/000703). For such semi-permanent multi dose inhalers with disposable drug containers, the requirements to prevent drug accumulation are even more strict.

Apart from applications through dry powder inhalers the compositions of the invention can be administered in aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with. Such atomiser is the Respimat® which is described, for example, in PCT patent applications Nos. WO 91/14468 and WO 97/12687, reference here is being made to the contents thereof.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes, the particles of the active ingredient as produced may be size reduced by conventional means eg by micronisation. The desired fraction may be separated out by air classification or sieving. Preferably, the particles will be crystalline.

Apart from applications through dry powder inhalers the compositions of the invention can also be administered in aerosols which operate via propellant gases or by means of so-called atomisers, via which solutions of pharmacologically-active substances can be sprayed under high pressure so that a mist of inhalable particles results. Such atomisers are described, for example, in WO 91/14468 and WO 97/12687.

Achieving high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose hemihydrate. Pressurized aerosol compositions will generally be filled into canisters fitted with a valve, especially a metering valve. Canisters may optionally be coated with a plastics material e.g. a fluorocarbon polymer as described in WO96/32150. Canisters will be fitted into an actuator adapted for buccal delivery.

The compositions of the invention can optionally comprise a therapeutically effective amount of one or more other therapeutic agents which are known to be useful in the treatment of respiratory disorders, such as PDE4 inhibitors, corticosteroids and/or anticholinergics.

The amount of each active which is required to achieve a therapeutic effect will, of course, vary with the particular active, the route of administration, the subject under treatment, and the particular disorder or disease being treated.

The active ingredients may be administered from 1 to 6 times a day, sufficient to exhibit the desired activity. Preferably, the active ingredients are administered once or twice a day, most preferably once a day.

Examples of suitable PDE4 inhibitors that can be combined with β2-agonists are benafentrine dimaleate, etazolate, denbufylline, rolipram, cipamfylline, zardaverine, arofylline, filaminast, tipelukast, tofimilast, piclamilast, tolafentrine, mesopram, drotaverine hydrochloride, lirimilast, roflumilast, cilomilast, oglemilast, apremilast, tetomilast, revamilast, ronomilast, (R)-(+)-4-[2-(3-Cyclopentyloxy-4-methoxyphenyl)-2-phenylethyl]pyridine (CDP-840), N-(3,5-Dichloro-4- pyridinyl)-2-[1-(4-fluorobenzyl)-5-hydroxy-1H-indol-3-yl]-2-oxoacetamide (GSK-842470), 9-(2-Fluorobenzyl)-N6-methyl-2-(trifluoromethyl)adenine (NCS-613), N-(3,5-Dichloro-4-pyridinyl)-8-methoxyquinoline-5-carboxamide (D-4418), 3-[3-(Cyclopentyloxy)-4-methoxybenzyl]-6-(ethylamino)-8-iso-propyl-3H-purine hydrochloride (V-11294A), 6-[3-(N,N-Dimethylcarbamoyl)-phenyl-sulfonyl]-4-(3-methoxyphenylamino)-8-methylquinoline-3-carboxamide hydrochloride (GSK-256066), 4-[6,7-Diethoxy-2,3-bis(hydroxymethyl)naphthalen-1-yl]-1-(2-methoxy-ethyl)pyridin-2(1H)-one (T-440), (−)-trans-2-[3'-[3-(N-Cyclopropylcarbamoyl)-4-oxo-1,4-dihydro-1,8-naphthyridin-1-yl]-3-fluorobiphenyl-4-yl]cyclopropanecarboxylic acid, MK-0873, CDC-801, GSK-356278, TA-7906, CP-80633, RPL-554, NIK-616, GPD-1116, D4396, UK-500001, BLX-914, 2-carbomethoxy-4-cyano-4-(3-cyclopropylmethoxy-4-difluoromethoxyphenyl)cyclohexan1-one, cis[4-cyano-4-(3-cyclopropylmethoxy-4-difluoromethoxyphenyl)cyclohexan-1-ol, 5(S)-[3-(Cyclopentyloxy)-4-methoxyphenyl]-3(S)-(3-methylbenzyl)piperidin-2-one (IPL-455903), ONO-6126 (Eur Respir J 2003, 22(Suppl. 45): Abst 2557) and the compounds claimed in the PCT patent applications number WO 03/097613, WO 2004/058729, WO 2005/049581, WO 2005/123693, WO 2005/123692, and WO 2010/069504.

Examples of suitable corticosteroids and glucocorticoids that can be combined with β2-agonists are prednisolone, methylprednisolone, dexamethasone, dexamethasone acetate, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone, mometasone furoate, rimexolone, prednisolone farnesylate, ciclesonide, butixocort propionate, RS-85095, CGP-13774, GW-250495, deltacortisone, NO-Prednisolone, NO-Budesonide, etiprednol dicloacetate, QAE-397, 7beta-OH-EPIA, RPR-106541, deprodone propionate, fluticasone, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, 21-Chloro-11beta-hydroxy-17alpha-[2-(methylsulfanyl)acetoxy]-4-pregnene-3,20-dione, des-isobutyryl-ciclesonide, hydrocortisone acetate, hydrocortisone sodium succinate, prednisolone sodium phosphate and hydrocortisone probutate, prednisolone sodium metasulfobenzoate and clobetasol propionate.

Examples of suitable M3 antagonists (anticholinergics) that can be combined with β2-agonists are tiotropium salts, oxitropium salts, flutropium salts, ipratropium salts, glycopyrronium salts, trospium salts, zamifenacin, revatropate, espatropate, darotropium bromide, CI-923, NPC-14695, BEA-2108, 3-[2-Hydroxy-2,2-bis(2-thienyl)acetoxy]-1-(3-phenoxypropyl)-1-azoniabicyclo[2.2.2]octane salts (in particular aclidinium salts, more preferably aclidinium bromide), 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3,3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenyl-acetamide (J-106366), 2(R)-Cyclopentyl-2-hydroxy-N-[1-(4-methyl-3-pentenyl)-4-piperidinyl]-2-phenylacetamide (J-104129), 1-[4-(2-Aminoethyl)piperidin-1-yl]-2(R)-[3,3-difluorocyclopent-1(R)-yl]-2-hydroxy-2-phenylethan-1-one (Banyu-280634), N—[N-[2-[N-[1-(Cyclohexylmethyl)piperidin-3(R)-ylmethyl]carbamoyl]ethyl]carbamoylmethyl]-3,3,3-triphenylpropionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), 3(R)-[4,4-Bis(4-fluorophenyl)-2-oxoimidazolidin-1-yl]-1-methyl-1-[2-oxo-2-(3-thienyl)ethyl]pyrrolidinium iodide, N-[1-(3-Hydroxybenzyl)-1-methylpiperidinium-3(S)-yl]-N—[N-[4-(isopropoxy-carbonyl)phenyl]carbamoyl]-L-tyrosinamide trifluoroacetate, UCB-101333, Merck's OrM3, 7-endo-(2-hydroxy-2,2-di phenylacetoxy)-9,9-di methyl-3-oxa-9-azoniatricyclo[3.3.1.0(2,4)]-nonane salts, 3(R)-[4,4-Bis(4-fluorophenyl)-2-oxoimidazolidin-1-yl]-1-methyl-1-(2-phenylethyl)pyrrolidinium iodide, trans-4-[2-[Hydroxy-2,2-(dithien-2-yl)acetoxy]-1-methyl-1-(2-phenoxyethyl)piperidinium bromide from Novartis (412682), 7-(2,2-diphenylpropionyloxy)-7,9,9-trimethyl-3-oxa-9-azoniatricyclo[3.3.1.0*2,4*]nonane salts, 7-hydroxy-7,9,9-trimethyl-3-oxa-9-azoniatricyclo[3.3.1.0*2,4*]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts. Among the salts chlorides, bromides, iodides and methanesulphonates are preferred.

Particularly preferred pharmaceutical composition according to the invention comprise a polymorphic crystal form as defined above and a therapeutically effective amount of one or more additional therapeutic agents selected from the group consisting of mometasone furoate, ciclesonide, budesonide, fluticasone propionate, fluticasone furoate, tiotropium salts, glycopyrronium salts, 3-[2-Hydroxy-2,2-bis(2-thienyl)acetoxy]-1-(3-phenoxypropyl)-1-azoniabicyclo[2.2.2]octane salts (in particular aclidinium salts, preferably aclidinium bromide), 1-(2-Phenylethyl)-3-(9H-xanthen-9-ylcarbonyloxy)-1-azoniabicyclo[2.2.2]octane salts, rolipram, roflumilast, cilomilast and the compounds claimed in the PCT patent applications number WO03/097613, WO2004/058729, WO 2005/049581, WO 2005/123693 and WO 2005/123692

Thus, in one aspect of the invention, the composition comprises a corticosteroid and a crystalline Type β and/or Hydrate polymorph. Particularly preferred corticosteroids are those selected from the group consisting of mometasone furoate, ciclesonide, budesonide, fluticasone furoate and fluticasone propionate.

In another aspect of the invention, the composition comprises an anticholinergic agent and a crystalline Type β and/or Hydrate polymorph. Particularly preferred anticholinergic agents are those selected from the group consisting of tiotropium salts, glycopirronium salts, 3-[2-Hydroxy-2,2-bis(2-thienyl)acetoxy]-1-(3-phenoxypropyl)-1-azoniabicyclo[2.2.2]-octane salts and 1-(2-Phenylethyl)-3-(9H-xanthen-9-ylcarbonyloxy)-1-azoniabicyclo[2.2.2]-octane salts. The composition may further comprise a corticosteroid selected from the group consisting of mometasone furoate, ciclesonide, budesonide, fluticasone furoate and fluticasone propionate.

In a still other aspect of the invention, the composition comprises a PDE4 inhibidor and a crystalline Type β and/or Hydrate polymorph. Particularly preferred PDE4 inhibidors are those selected from the group consisting of rolipram, roflumilast, cilomilast and the compounds claimed in the PCT patent applications number WO03/097613, WO2004/058729, WO 2005/049581, WO 2005/123693 and WO 2005/123692. The composition may further comprise a corticosteroid selected from the group consisting of mometasone furoate, ciclesonide, budesonide, fluticasone furoate and fluticasone propionate. In addition to the salt of the invention and to the PDE4 inhibitor, the composition may further comprise an anticholinergic agent selected from the group consisting of tiotropium salts, glycopirronium salts, 3-[2-Hydroxy-2,2-bis(2-thienyl)acetoxy]-1-(3-phenoxypropyl)-1-azoniabicyclo[2.2.2]octane salts and 1-(2-Phenylethyl)-3-(9H-xanthen-9-ylcarbonyloxy)-1-azoniabicyclo[2.2.2]octane salts.

In a particularly preferred embodiment of the present invention, the composition comprises a crystalline Type β and/or Hydrate polymorph and a therapeutically effective amount of a 3-[2-hydroxy-2,2-bis(2-thienyl)acetoxy]-1-(3-phenoxypropyl)-1-azoniabicyclo[2.2.2]octane salts. Optionally, the composition further comprises a corticosteroid and/or a PDE4 inhibidor.

In another particularly preferred embodiment of the present invention, the composition comprises a crystalline Type β and/or Hydrate polymorph and a therapeutically effective amount of mometasone furoate. Optionally, the composition further comprises an anticholinergic and/or a PDE4 inhibidor.

In yet another embodiment of the invention, the composition comprises a crystalline Type β and/or Hydrate polymorph, a corticosteroid, an anticholinergic agent and a PDE4 inhibidor.

The crystalline polymorphic salts of the present invention and the combinations of the invention may be used in the treatment of respiratory diseases, wherein the use of bronchodilating agents is expected to have a beneficial effect, for example asthma, acute or chronic bronchitis, emphysema, or Chronic Obstructive Pulmonary Disease (COPD).

The active crystalline polymorphic salts in the combination, i.e. the β2-agonist of the invention and the PDE4 inhibitors, corticosteroids or glucocorticoids and/or anticholinergics may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be taken in the morning and the other (s) later in the day. Or in another scenario, one or two actives could be taken twice daily and the other (s) once daily, either at the same time as one of the twice-a-day dosing occurred, or separately. Preferably at least two, and more preferably all, of the actives would be taken together at the same time. Preferably, at least two, and more preferably all actives would be administered as an admixture.

The active substance compositions according to the invention are preferably administered in the form of compositions for inhalation delivered with the help of inhalers, especially dry powder inhalers; however, any other form of topical, parenteral or oral application is possible. Here, the application of inhaled compositions embodies the preferred application form, especially in the therapy of obstructive lung diseases or for the treatment of asthma.

Additional suitable carriers for formulations of the active salts of the present invention can be found in Remington: The Science and Practice of Pharmacy, 20th Edition, Lippincott Williams & Wilkins, Philadelphia, Pa., 2000. The following non-limiting examples illustrate representative pharmaceutical compositions of the invention.

Formulation Example 1

Gelatin Cartridge for Inhalation

| Ingredient | Amount |
| --- | --- |
| 5-(2-{[6-(2,2-difluoro-2-phenylethoxy)hexyl]amino}-1(R)-hydroxyethyl)-8-hydroxyquinolin-2(1H)-one, napadisylate (micronized) | 0.2 mg |
| Lactose | 25 mg |

Formulation Example 2

Formulation for Inhalation with a DPI

| Ingredient | Amount |
| --- | --- |
| 5-(2-{[6-(2,2-difluoro-2-phenylethoxy)hexyl]amino}-1(R)-hydroxy-ethyl)-8-hydroxyquinolin-2(1H)-one, napadisylate (micronized) | 15 mg |
| Lactose | 3000 mg |

Formulation Example 3

Formulation for Inhalation with a DPI

| Ingredient | Amount |
| --- | --- |
| 5-(2-{[6-(2,2-difluoro-2-phenylethoxy)hexyl]amino}-1(R)-hydroxy-ethyl)-8-hydroxyquinolin-2(1H)-one, napadisylate (micronized) | 15 mg |
| 3(R)-[2-Hydroxy-2,2-bis(2-thienyl)acetoxy]-1-(3-phenoxypropyl)-1-azoniabicyclo[2.2.2]octane bromide | 100 mg |
| Lactose | 3000 mg |

Formulation Example 4

Formulation for Inhalation with a DPI

| Ingredient | Amount |
| --- | --- |
| 5-(2-{[6-(2,2-difluoro-2-phenylethoxy)hexyl]amino}-1(R)-hydroxy-ethyl)-8-hydroxyquinolin-2(1H)-one, napadisylate (micronized) | 15 mg |
| Mometasone furoate | 400 mg |
| Lactose | 3000 mg |

Formulation Example 5

Formulation for Inhalation with a DPI

| Ingredient | Amount |
|---|---|
| 5-(2-{[6-(2,2-difluoro-2-phenylethoxy)hexyl]amino}-1(R)-hydroxy-ethyl)-8-hydroxyquinolin-2(1H)-one, napadisylate (micronized) | 15 mg |
| 3(R)-[2-Hydroxy-2,2-bis(2-thienyl)acetoxy]-1-(3-phenoxypropyl)-1-azoniabicyclo[2.2.2]octane bromide | 100 mg |
| Mometasone furoate | 400 mg |
| Lactose | 3000 mg |

Formulation Example 6

Formulation for a MDI

| Ingredient | Amount |
|---|---|
| 5-(2-{[6-(2,2-difluoro-2-phenylethoxy)hexyl]amino}-1(R)-hydroxy-ethyl)-8-hydroxyquinolin-2(1H)-one, napadisylate (micronized) | 10 g |
| 1,1,1,2,3,3,3-heptafluoro-n-propane | q.s. to 200 ml |

The invention claimed is:

1. A crystalline polymorph of 5-(2-{[6-(2,2-difluoro-2-phenylethoxy)hexyl]amino}-1(R)-hydroxyethyl)-8-hydroxyquinolin-2(1H)-one heminapadisylate, which is chosen from (i) a hydrate polymorph, or (ii) a type β polymorph prepared by drying said hydrate polymorph,
wherein:
the hydrate polymorph has:
a) an X-Ray Powder Diffraction (XRPD) pattern with peaks at 13.3, 16.1 and 19.2 degrees 2θ (±0.1 degrees 2θ); and
b) a Differential Scanning Calorimetry (DSC) pattern with a first endotherm in the range of 75-120° C. (±5° C.) and a second endotherm with an onset at 190° C. (±1° C.),
the type β polymorph has:
a) an X-Ray Powder Diffraction (XRPD) pattern with a peak at 19.1 degrees 2θ (±0.1 degrees 2θ); and
b) a Differential Scanning Calorimetry (DSC) pattern with a first endotherm with an onset at 190° C. (±1° C.).

2. The crystalline polymorph according to claim 1, wherein the hydrate polymorph is prepared by:
a) adding a solution of naphthalene-1,5-disulfonic acid tetrahydrate in methanol/acetic acid (1:1) to a solution of 5-(2-{[6-(2,2-difluoro-2-phenylethoxy)hexyl]amino}-1(R)-hydroxyethyl)-8-hydroxyquinolin-2(1H)-one in methanol/acetic acid (1:1) to form a reaction mixture,
b) stirring the reaction mixture at reflux for 30 minutes and allowing the reaction mixture to cool down to 20-25° C., then stirring at 20-25° C. for 20 hours,
c) isolating by filtrating and washing with methanol, and drying at 50° C. to obtain the hydrate polymorph.

3. The crystalline polymorph according to claim 1, wherein the crystalline polymorph is the hydrate polymorph and the X-Ray Powder Diffraction (XRPD) pattern has at least one additional peak chosen from at 9.9, 11.5, 12.7, 14.4, 15.2, 16.7, 19.6, 20.2, 21.9, 22.7, 23.1, 24.2, 25.6, 27.0, 27.6, 28.9, 30.5, 31.7, 33.4, or 37.0 degrees 2θ (±0.1 degrees 2θ).

4. The crystalline polymorph according claim 1, wherein the crystalline polymorph is the hydrate polymorph and wherein the X-Ray Powder Diffraction (XRPD) pattern has peaks at 9.9, 11.5, 12.7, 13.3, 14.4, 15.2, 16.1, 16.7, 19.2, 19.6, 20.2, 21.9, 22.7, 23.1, 24.2, 25.6, 27.0, 27.6, 28.9, 30.5, 31.7, 33.4, or 37.0 degrees 2θ (±0.1 degrees 2θ).

5. The crystalline polymorph according to claim 1, wherein the crystalline polymorph is the hydrate polymorph having:
a) an X-Ray powder diffraction (XRPD) pattern substantially in accordance with FIG. 5, and/or
b) a Differential Scanning Calorimetry (DSC) pattern substantially in accordance with FIG. 6.

6. The crystalline polymorph according to claim 1, wherein the crystalline polymorph is the type β polymorph and is prepared by drying the hydrate polymorph at 105° C. for 20 hours.

7. The crystalline polymorph according to claim 1, wherein the crystalline polymorph is the type β polymorph and wherein the X-ray powder diffraction (XRPD) pattern has at least one additional peak chosen from at 10.0, 11.6, 12.7, 13.5, 14.5, 16.1, 19.7, 20.3, 22.0, 22.8, 23.8, 24.2, 25.8, 27.1, 27.7, 29.2, or 39.4 degrees 2θ (±0.1 degrees 2θ).

8. The crystalline polymorph according to claim 1, wherein the crystalline polymorph is the type β polymorph and wherein the X-ray powder diffraction (XRPD) pattern has peaks at 10.0, 11.6, 12.7, 13.5, 14.5, 16.1, 19.1, 19.7, 20.3, 22.0, 22.8, 23.8, 24.2, 25.8, 27.1, 27.7, 29.2, and 39.4 degrees 2θ (±0.1 degrees 2θ).

9. The crystalline polymorph according to claim 1, wherein the crystalline polymorph is the type 13 polymorph having:
a) an X-Ray powder diffraction (XRPD) pattern substantially in accordance with FIG. 1; and/or
b) a Differential Scanning Calorimetry (DSC) pattern substantially in accordance with FIG. 2.

10. A type 13 crystalline polymorph of 5-(2-{[6-(2,2-difluoro-2-phenylethoxy)hexyl]amino}-1(R)-hydroxyethyl)-8-hydroxyquinolin-2(1H)-one heminapadisylate, having:
a) an X-Ray Powder Diffraction (XRPD) pattern with peaks at 19.1, 19.7 and 22.8 degrees 2θ (±0.1 degrees 2θ); and
b) a Differential Scanning Calorimetry (DSC) pattern which shows a first endotherm with an onset at 190° C. (±1° C.).

11. The type 13 crystalline polymorph according to claim 10, having:
a) an X-Ray Powder Diffraction (XRPD) pattern having at least one additional peak chosen from at 10.0, 11.6, 12.7, 13.5, 14.5, 16.1, 19.7, 20.3, 22.0, 22.8, 23.8, 24.2, 25.8, 27.1, 27.7, 29.2, or 39.4 degrees 2θ (±0.1 degrees 2θ); and/or
b) a Differential Scanning Calorimetry (DSC) pattern substantially in accordance with FIG. 2.

12. The crystalline polymorph according to claim 1, wherein the crystalline polymorph is the hydrate polymorph and
wherein the hydrate polymorph is isolated in a pure form or is admixed with a polymorph selected from the type β polymorph and a type α polymorph.

13. The crystalline polymorph according to claim 1, wherein the crystalline polymorph is the type β polymorph and,
wherein the type β polymorph is isolated in a pure form or is admixed with a polymorph chosen from the hydrate polymorph and a type α polymorph.

14. A pharmaceutical composition comprising a therapeutically effective amount of the crystalline polymorph according to claim 1 and a pharmaceutically acceptable carrier.

15. The pharmaceutical composition according to claim 14, wherein the composition is formulated for administration by inhalation.

16. The pharmaceutical composition according to claim 15, comprising less than 0.1 wt % of an additive for improving the Fine Particle Fraction (FPF).

17. The pharmaceutical composition of claim 14, wherein the composition further comprises a therapeutically effective amount of at least one other therapeutic agent.

18. The pharmaceutical composition of claim 17, wherein the at least one other therapeutic agent is chosen from a corticosteroid, an anticholinergic agent, or a PDE4 inhibitor.

19. The pharmaceutical composition of claim 17 wherein the at least one other therapeutic agent is a corticosteroid selected from the group consisting of prednisolone, methylprednisolone, dexamethasone, dexamethasone acetate, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone, mometasone furoate, rimexolone, prednisolone farnesylate, ciclesonide, butixocort propionate, RS-85095, CGP-13774, GW-250495, deltacortisone, NO-Prednisolone, NO-Budesonide, etiprednol dicloacetate, QAE-397, 7beta-OH-EPIA, RPR-106541, deprodone propionate, fluticasone, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, 21-Chloro-11beta-hydroxy-17alpha-[2-(methylsulfanyl)acetoxy]-4-pregnene-3,20-dione, des-isobutyrylciclesonide, hydrocortisone acetate, hydrocortisone sodium succinate, prednisolone sodium phosphate and hydrocortisone probutate, prednisolone sodium metasulfobenzoate, and clobetasol propionate.

20. The pharmaceutical composition of claim 17 wherein the at least one other therapeutic agent is an anticholinergic agent selected from the group consisting of tiotropium salts, oxitropium salts, flutropium salts, ipratropium salts, glycopyrronium salts, trospium salts, zamifenacin, revatropate, espatropate, darotropium bromide, CI-923, NPC-14695, BEA-2108, 3-[2-Hydroxy-2,2-bis(2-thienyl)acetoxy]-1-(3-phenoxypropyl)-1-azoniabicyclo[2.2.2]octane salts (in particular aclidinium salts, more preferably aclidinium bromide), 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3,3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenyl-acetamide (J-106366), 2(R)-Cyclopentyl-2-hydroxy-N-[1-(4-methyl-3-pentenyl)-4-piperidinyl]-2-phenylacetamide (J-104129), 1-[4-(2-Aminoethyl) piperidin-1-yl]-2(R)-[3,3-difluorocyclopent-1(R)-yl]-2-hydroxy-2-phenylethan-1-one (Banyu-280634), N—[N-[2-[N-[1-(Cyclohexylmethyl)piperidin-3(R)-ylmethyl] carbamoyl]ethyl]carbamoylmethyl]-3,3,3-triphenylpropionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), 3(R)-[4,4-Bis(4-fluorophenyl)-2-oxoimidazolidin-1-yl]-1-methyl-1-[2-oxo-2-(3-thienyl)ethyl]pyrrolidinium iodide, N-[1-(3-Hydroxybenzyl)-1-methylpiperidinium-3(S)-yl]-N—[N-[4-(isopropoxy-carbonyl)phenyl]carbamoyl]-L-tyrosinamide trifluoroacetate, UCB-101333, Merck's OrM3, 7-endo-(2-hydroxy-2,2-diphenylacetoxy)-9,9-dimethyl-3-oxa-9-azoniatricyclo[3.3.1.0(2,4)]-nonane salts, 3(R)[4,4-Bis(4-fluorophenyl)-2-oxoimidazolidin-1-yl]-1-methyl-1-(2-phenylethyl)pyrrolidinium iodide, trans-4-[2-[Hydroxy-2,2-(dithien-2-yl)acetoxy]-1-methyl-1-(2-phenoxyethyl) piperidinium bromide from Novartis (412682), 7-(2,2-diphenylpropionyloxy)-7,9,9-trimethyl-3-oxa-9-azoniatricyclo[3.3.1.0*2,4*]nonane salts, 7-hydroxy-7,9,9-trimethyl-3-oxa-9-azoniatricyclo[3.3.1.0*2,4*]nonane 9-methyl-9H-fluorene-9-carboxylic acid ester salts, and pharmacologically-compatible acid addition salts thereof
or at least one racemate, enantiomer, diastereomer or mixture thereof.

21. The pharmaceutical composition of claim 17 wherein the at least one other therapeutic agent is a PDE4 inhibitor selected from the group consisting of benafentrine dimaleate, etazolate, denbufylline, rolipram, cipamfylline, zardaverine, arofylline, filaminast, tipelukast, tofimilast, piclamilast, tolafentrine, mesopram, drotaverine hydrochloride, lirimilast, roflumilast, cilomilast, oglemilast, apremilast, tetomilast, revamilast, ronomilast, (R)-(+)-4-[2-(3-Cyclopentyloxy-4-methoxyphenyl)-2-phenylethyl]pyridine (CDP-840), N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N6-methyl-2-(trifluoromethyl)adenine (NCS-613), N-(3,5-Dichloro-4-pyridinyl)-8-methoxyquinoline-5-carboxamide (D-4418), 3-[3-(Cyclopentyloxy)-4-methoxybenzyl]-6-(ethylamino)-8-iso-propyl-3H-purine hydrochloride (V-11294A), 6-[3-(N,N-Dimethylcarbamoyl)-phenyl-sulfonyl]-4-(3-methoxyphenylamino)-8-methylquinoline-3-carboxamide hydrochloride (GSK-256066), 4-[6,7-Diethoxy-2,3-bis(hydroxymethyl)naphthalen-1-yl]-1-(2-methoxy-ethyl)pyridin-2(1H)-one (T-440), (−)-trans-2-[3'-[3-(N-Cyclopropylcarbamoyl)-4-oxo-1,4-dihydro-1,8-naphthyridin-1-yl]-3-fluorobiphenyl-4-yl] cyclopropanecarboxylic acid, MK-0873, CDC-801, GSK-356278, TA-7906, CP-80633, RPL-554, NIK-616, GPD-1116, D4396, UK-500001, BLX-914, 2-carbomethoxy-4-cyano-4-(3-cyclopropylmethoxy-4-difluoromethoxyphenyl)cyclohexan1-one, cis[4-cyano-4-(3-cyclopropylmethoxy-4-difluoromethoxyphenyl) cyclohexan-1-ol, and 5(S)-[3-(Cyclopentyloxy)-4-methoxyphenyl]-3(S)-(3-methylbenzyl)piperidin-2-one (IPL-455903).

22. The pharmaceutical composition according to claim 17 wherein the at least one other therapeutic agent is selected from the group consisting of mometasone furoate, ciclesonide, budesonide, fluticasone propionate, fluticasone furoate, tiotropium salts, glycopirrolium salts, 3-[2-Hydroxy-2,2-bis(2-thienyl)acetoxy]-1-(3-phenoxypropyl)-1-azoniabicyclo[2.2.2]octane salts, 1-(2-Phenylethyl)-3-(9H-xanthen-9-ylcarbonyloxy)-1-azoniabicyclo[2.2.2]octane salts, rolipram, roflumilast, and cilomilast.

23. A combination comprising a crystalline polymorph according to claim 1 and at least one other therapeutic agent chosen from a corticosteroid, an anticholinergic agent, or a PDE4 inhibitor.

24. A method of treating a pulmonary disease in a mammal associated with β2 adrenergic receptor activity, the method comprising administering to the mammal, a therapeutically effective amount of a pharmaceutical composition according to claim 14.

25. The method of claim 24 wherein the pulmonary disease is asthma or chronic obstructive pulmonary disease.

26. The method according to claim 24 further comprising administering a therapeutically effective amount of at least one other therapeutic agent chosen from a corticosteroid, an anticholinergic agent, or a PDE4 inhibitor.

27. The crystalline polymorph according to claim 2, wherein the drying step is conducted in vacuum.

28. The crystalline polymorph according to claim 6, wherein the crystalline polymorph is prepared by drying the hydrate polymorph at 105° C. for 20 hours in a vacuum.

29. The type 13 crystalline polymorph according to claim 10, having:
   a) an X-Ray Powder Diffraction (XRPD) pattern having at least one additional peak chosen from at 10.0, 11.6, 12.7, 13.5, 14.5, 16.1, 19.7, 20.3, 22.0, 22.8, 23.8, 24.2, 25.8, 27.1, 27.7, 29.2 or 39.4 degrees 2θ (±0.1 degrees 2θ); and/or
   b) a Differential Scanning Calorimetry (DSC) pattern substantially in accordance with FIG. 2.

30. The type 13 crystalline polymorph according to claim 10, having:
   a) an X-Ray Powder Diffraction (XRPD) pattern substantially in accordance with FIG. 1; and/or
   b) a Differential Scanning Calorimetry (DSC) pattern substantially in accordance with FIG. 2.

31. A method of treating a pulmonary disease in a mammal associated with β2 adrenergic receptor activity, comprising administering to the mammal a therapeutically effective amount of a crystalline polymorph according to claim 1.

* * * * *